United States Patent [19]
Segev

[11] Patent Number: 5,846,709
[45] Date of Patent: Dec. 8, 1998

[54] CHEMICAL PROCESS FOR AMPLIFYING AND DETECTING NUCLEIC ACID SEQUENCES

[75] Inventor: David Segev, D. N. Evtah, Israel

[73] Assignee: ImClone Systems Incorporated, New York, N.Y.

[21] Appl. No.: 77,251

[22] Filed: Jun. 15, 1993

[51] Int. Cl.$^6$ .............................. C12Q 1/68; C12P 19/34
[52] U.S. Cl. .............................................. 435/6; 435/91.2
[58] Field of Search ........................ 435/6, 91.2; 935/8; 536/23.1, 24.3, 25.3, 25.6

[56] References Cited

U.S. PATENT DOCUMENTS

| | | | |
|---|---|---|---|
| 4,638,195 | 1/1987 | Mullis et al. | 435/6 |
| 5,185,243 | 2/1993 | Ullman et al. | 435/6 |

FOREIGN PATENT DOCUMENTS

| | | |
|---|---|---|
| 320 308 | 6/1989 | European Pat. Off. . |
| 552 931 | 7/1993 | European Pat. Off. . |
| WO 90/01069 | 2/1990 | WIPO . |

*Primary Examiner*—James Martinell
*Attorney, Agent, or Firm*—Irving N. Feit; Thomas C. Gallagher; Eric J. Sheets

[57] ABSTRACT

The present invention is directed to a method of amplifying and detecting single or double stranded target nucleic acid molecules. Amplification of the target nucleic acid molecule is accomplished by using at least two chemically modified oligonucleotide probes per target nucleic acid molecule to form a joined oligonucleotide product. Each oligonucleotide probe is comprised of a long and short sequence. The long sequence of each probe hybridizes to adjacent regions of the target nucleic acid molecule. The short sequences of each probe hybridize to each other. Chemical functionality groups attached to the short sequences of each oligonucleotide probe covalently combine linking the probes to form a joined oligonucleotide product. The joined oligonucleotide product is formed without the use of enzymes.

The reactivity of the chemical functionality groups on each probe is target dependent. The chemical functionality group on each probe is prevented from reacting with other chemical functionality groups on other probes unless the probes are properly hybridized to the target molecule and to each other, as described above. The chemical functionality groups are covalently attached to the short sequence of each probe in such a way that they are sheltered or protected from the chemical functionality groups of other probes while the probes are in solution. Only when the short sequences of adjacent probes are hybridized to each other are the chemical functionality groups on the probes brought into close enough proximity to form a covalent bond and join the probes to form a joined oligonucleotide product.

26 Claims, 20 Drawing Sheets

FIG - 1
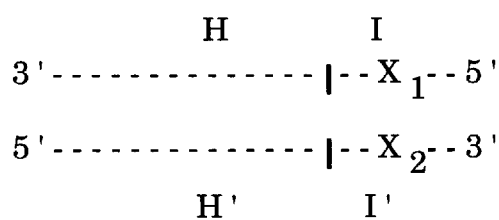
Probe 1
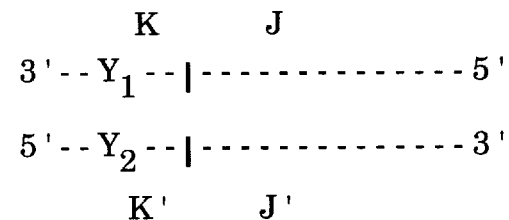
Probe 2
Probe 1'
Probe 2'

FIG - 2
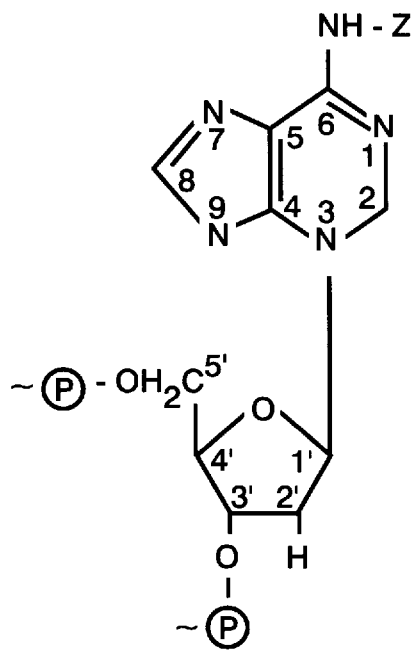
$A_1$
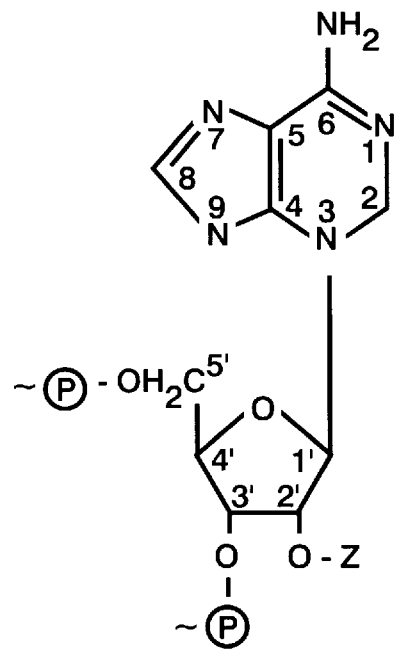
$A_2$
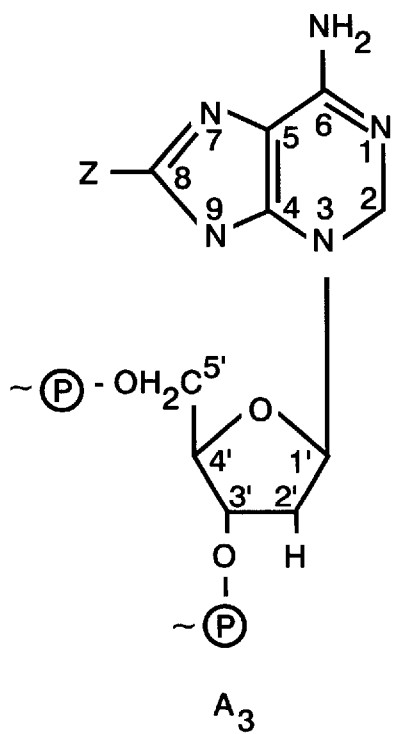
$A_3$
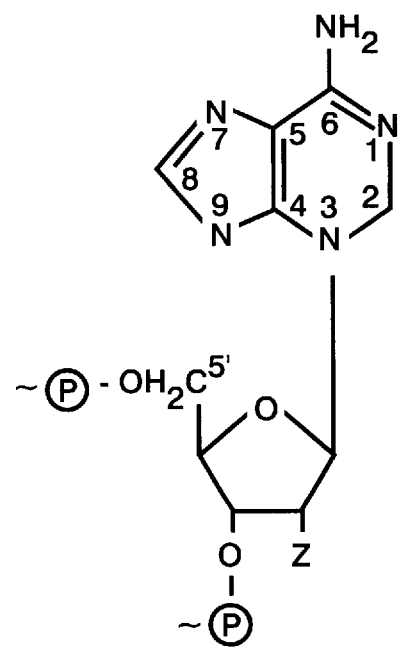
$A_4$

FIG - 3
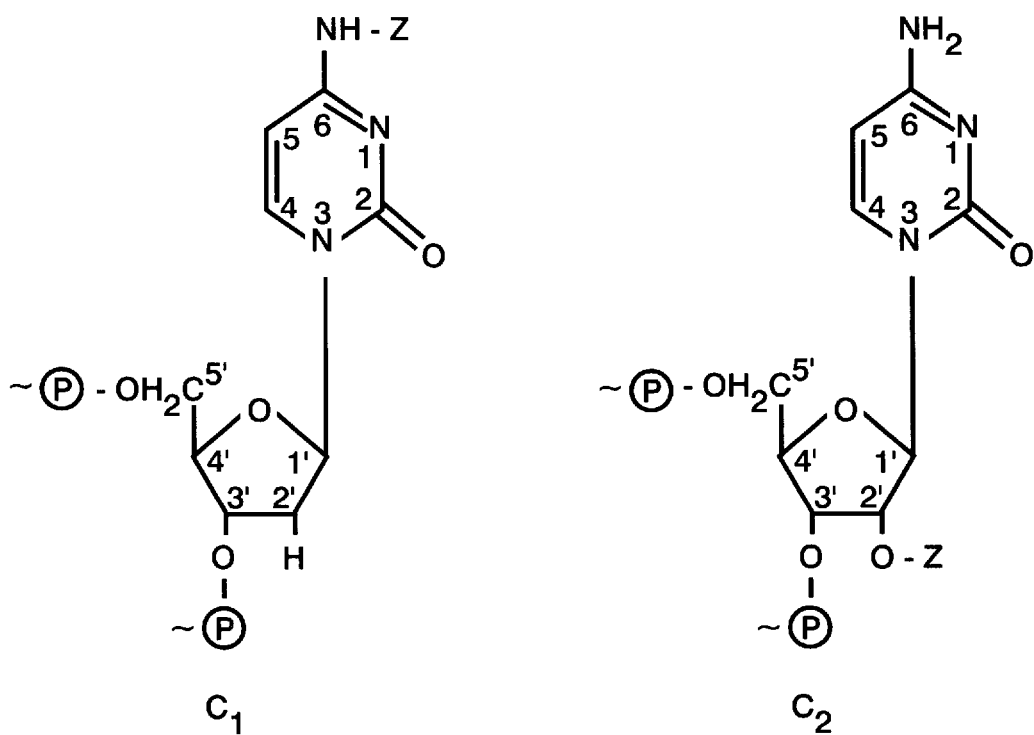
$C_1$
$C_2$
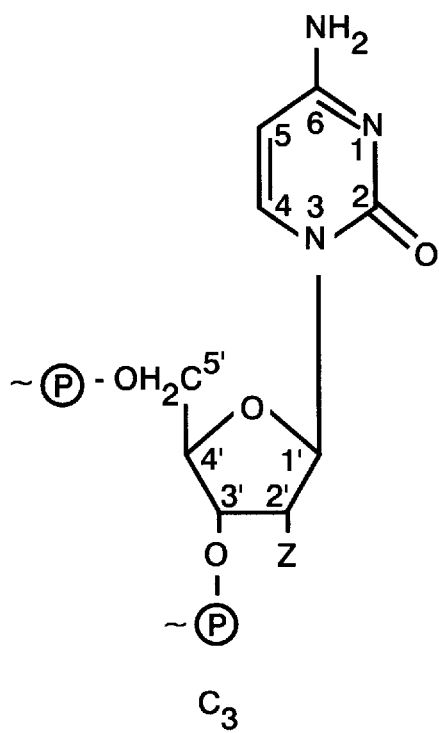
$C_3$

FIG - 5
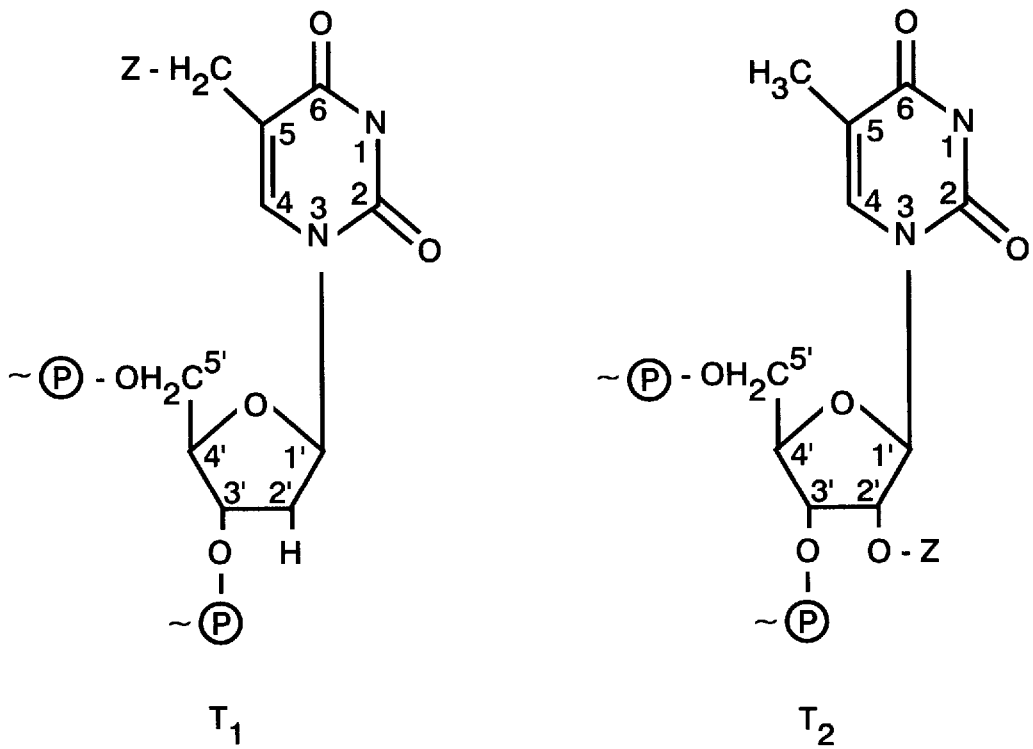
$T_1$          $T_2$
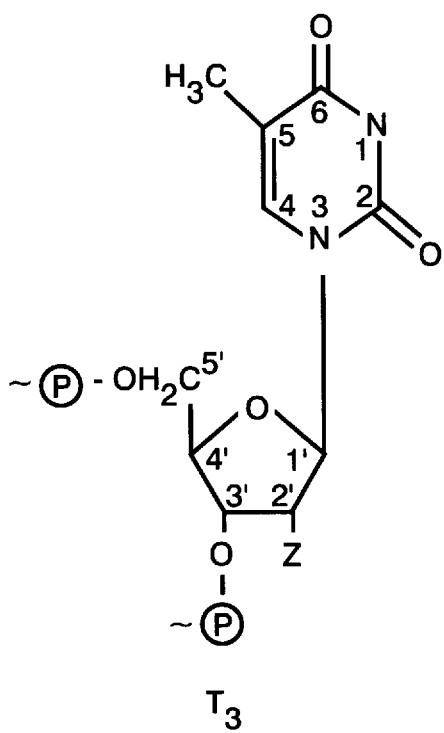
$T_3$

Probe 1

Probe 2

FIG - 7.1
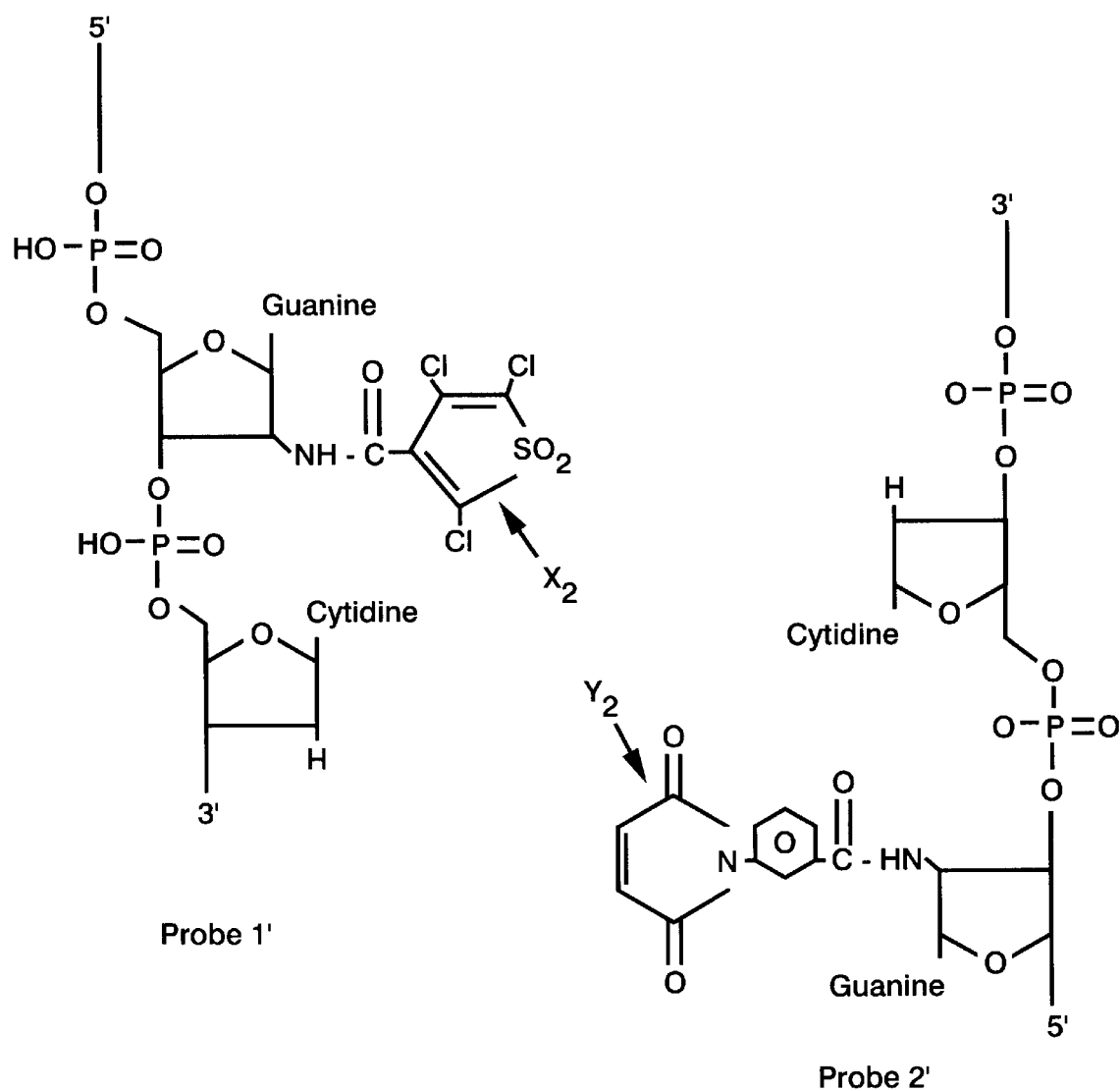

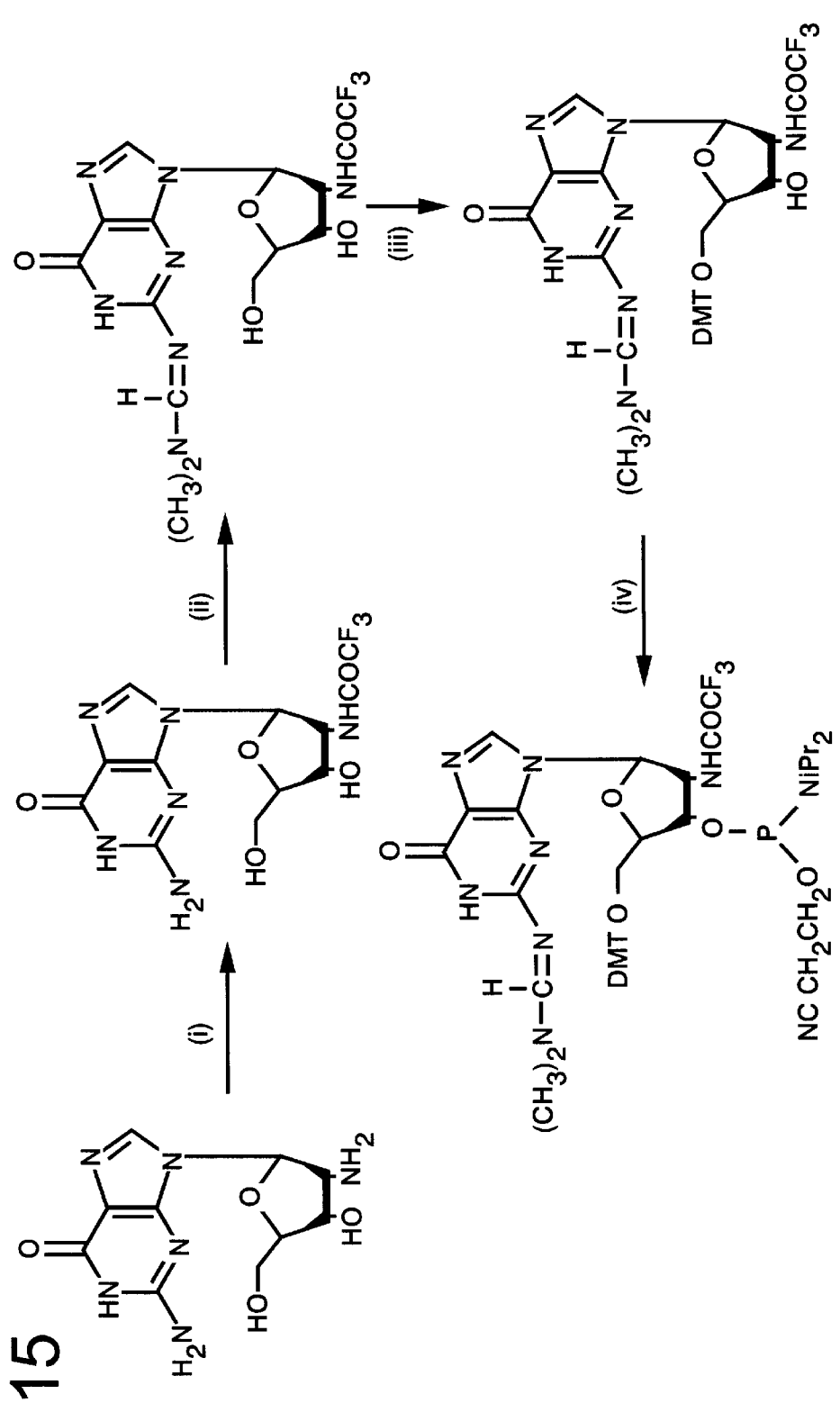

FIG-15 Reaction scheme for the preparation of protected 2'-amino-2'-deoxyguanosine phosphoramidite. Reagents: i, S-ethyl-trifluorothioacetate in methanol; ii, dimethyl-formamide dimethylacetal in methanol; iii, dimethoxytrityl chloride, triethylamine in pyridine; iv, β-cyanoethyl (N,N-diisopropylamino) chlorophosphoramidite and N,N-diisopropyl-ethylamine in dichloromethane.

FIG - 16
Target sequence
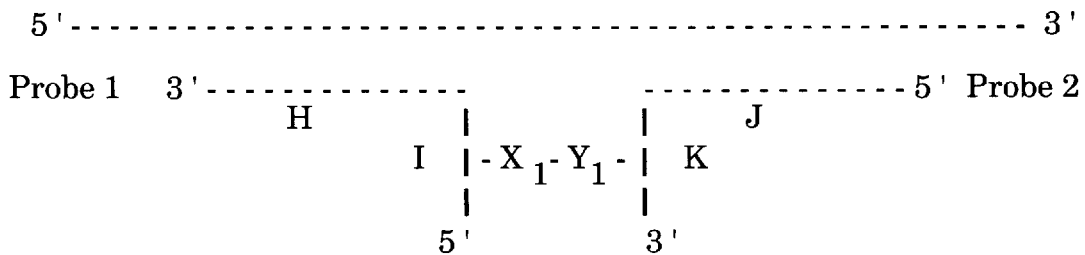
Denaturation of the first joined oligonucleotide product from the target sequence.
Target sequence
+
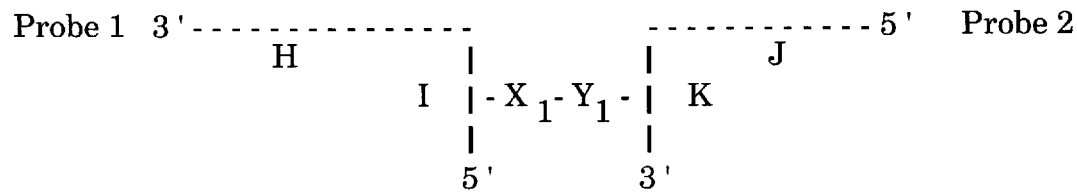
First Joined Oligonucleotide Product

FIG - 19
Second Joined Oligonucleotide Product
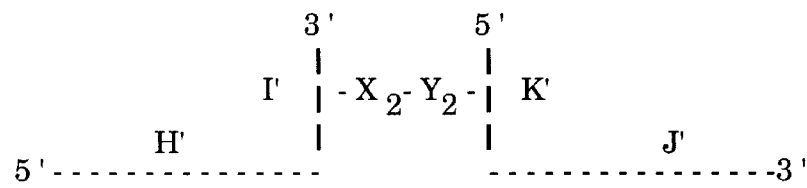
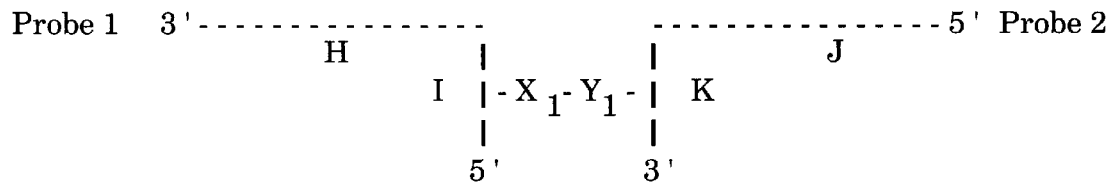
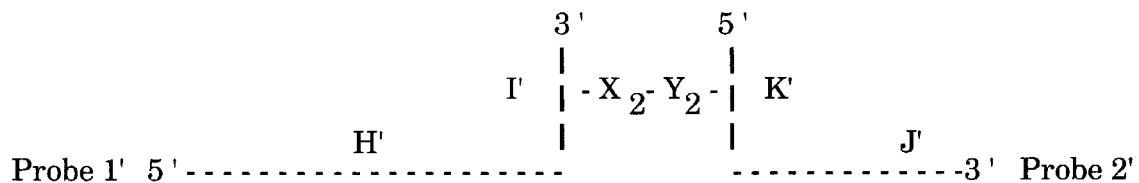
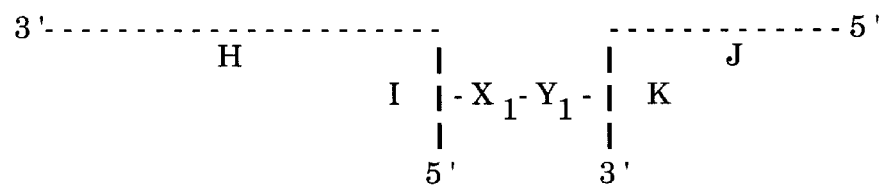
First Joined Oligonucleotide Product

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Human papillomavirus
        ( B ) STRAIN: type 16

( x i ) SEQUENCE DESCRIPTION: SEQ ID NO:1:

TTGTTGATAC TACACGCAGT ACAAATATGT CATTATGTGC TGCCATAT          48

( 2 ) INFORMATION FOR SEQ ID NO:2:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Human papillomavirus
        ( B ) STRAIN: type 16

( x i ) SEQUENCE DESCRIPTION: SEQ ID NO:2:

ATATGGCAGC ACATAATGAC ATATTTGTAC TGCGTGTAGT ATCAACAA          48

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

AATAGCATTG TACTGCGTGT AGTATCAACA A          31

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

ATATGGCAGC ACATAATGAC ATATTGCTAT T  31

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

TTGTTGATAC TACACGCAGT ACAATGCTAT T  31

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

AATAGCAATA TGTCATTATG TGCTGCCATA T  31

CHEMICAL PROCESS FOR AMPLIFYING AND DETECTING NUCLEIC ACID SEQUENCES

FIELD OF THE INVENTION

The present invention relates to a method for amplifying and detecting existing nucleic acid sequences in a test sample.

BACKGROUND OF THE INVENTION

The standard method for amplifying and detecting target nucleic acid sequences is the polymerase chain reaction (PCR). (See Saiki et al. in Science 239, 487 (1988) and Mullis et al in U.S. Pat. No. 4,683,195) A problem with PCR is non-specific polymerization leading to spurious background signals.

Backman et al., EP 320 308, disclose an alternative method, known as the ligase chain reaction (LCR), for amplifying a target nucleic acid sequence. In LCR, four nucleic acid probes are employed in excess. The first and third probes form a complementary oligonucleotide pair. The second and fourth probes form another complementary oligonucleotide pair. The first and second probes hybridize to sequences that are contiguous in the first strand of the target molecule. When hybridized, the first and second probes abut one another in a 5' phosphate-3' hydroxyl relationship, so that a ligase can join the two probes into a first fused product. Also, the third and fourth probes hybridize to sequences that are contiguous in the second strand of the target molecule. When hybridized, the third and fourth probes abut one another in a 5' phosphate-3' hydroxyl relationship, so that a ligase can join the two probes into a second fused product.

The first and second fused products are separated from the target strands, in effect doubling the target population in the sample. The fused products then serve as templates for further LCR reactions by hybridizing to their complement probes. As the cycle of hybridization, ligation and denaturation is repeated, the population of fused probes increases at a geometric rate. The fused probes are detected by standard methods.

These amplification reactions permit rapid analysis or characterization of sequences of interest, even where the starting amounts of material are extremely small. However, it is important that the amplification process be highly specific, since the amplification of untargeted sequences along with the target signal impairs the reliability of the amplification process.

As with PCR, a problem associated with LCR is undesirable background signal caused by target-independent ligation of the complementary oligonucleotide pairs. The undesirable background is due to the ability of these complementary pairs, which are added in excess, to cross-hybridize among themselves. Such cross-hybridization can lead to independent ligation of the probes to form joined products in the absence of the target sequence. These target-independent products are indistinguishable from the desired amplified target sequence.

Both PCR and LCR have additional drawbacks due to the requirement of polymerases or ligases in order to achieve amplification. In addition to being expensive, such enzymes exhibit lot-to-lot variations in activity and in the concentration of undesired nuclease contaminants. Such variations detract further from the reliability of the methods.

The problem to be solved by the present invention is to provide a method of amplification and detection of target sequences that uses neither polymerase nor ligase, and that reduces spurious background signals and improve reliability.

SUMMARY OF THE INVENTION

These and other objectives, as will become apparent to those with skill in the art, have been met by providing a process for amplifying and detecting, in a sample, a single stranded target nucleic acid molecule comprising a target sequence, or a double stranded nucleic acid target molecule comprising a target sequence and target complementary sequence, the process comprising the steps of:

(a) providing a first oligonucleotide complement pair and a second oligonucleotide complement pair, wherein:

(i) the first oligonucleotide complement pair consists of a probe 1 and a probe 1' and the second oligonucleotide complement pair consists of a probe 2 and a probe 2';

(ii) probe 1 comprises a long sequence H and a short sequence I; probe 1' comprises a long sequence H' and a short sequence I';

(iii) probe 2 comprises a long sequence J and a short sequence K; probe 2' comprises a long sequence J' and a short sequence K';

(iv) long sequence H of probe 1 and long sequence H' of probe 1' are complementary to each other;

(v) long sequence J of probe 2 and long sequence J' of probe 2' are complementary to each other;

(vi) long sequence H of probe 1 and long sequence J of probe 2 are complementary to adjacent portions of the target sequence;

(vii) long sequence H' of probe 1' and long sequence J' of probe 2' are complementary to adjacent portions of the target complementary sequence;

(viii) short sequence I and short sequence K do not hybridize to the target sequence when long sequence H and long sequence J hybridize to the target sequence;

(ix) short sequence I' and short sequence K' do not hybridize to the target complementary sequence when long sequence H' and long sequence J' hybridize to the target complementary sequence;

(x) short sequence I of probe 1 is complementary to short sequence K of probe 2 and short sequence I' of probe 1' is complementary to short sequence K' of probe 2';

(xi) the sugar or base moiety of one or more nucleotides of sequence I of probe 1 is modified with chemical functionality group $X_1$; the sugar or base moiety of one or more nucleotides of sequence K of probe 2 is modified with chemical functionality group $Y_1$; chemical functionality group $X_1$ is reactive with chemical functionality group $Y_1$;

(xii) the sugar or base moiety of one or more nucleotides of sequence I' of probe 1' is modified with chemical functionality group $X_2$; the sugar or base moiety of one or more nucleotides of sequence K' of probe 2' is modified with chemical functionality group $Y_2$; chemical functionality group $X_2$ is reactive with chemical functionality group $Y_2$;

(xiii) short sequence I hybridizes to short sequence K when long sequence H of probe 1 and long sequence J of probe 2 hybridize to adjacent portions of the target sequence;

(xiv) when short sequence I hybridizes to short sequence K, chemical functionality group $X_1$ reacts with chemical functionality group $Y_1$ to form a chemical bond;

(xv) short sequence I' hybridizes to short sequence K' when long sequence H' of probe 1' and long sequence J' of probe 2' hybridize to adjacent portions of a target complementary sequence;

(xvi) when short sequence I' hybridizes to short sequence K', chemical functionality group $X_2$ reacts with chemical functionality group $Y_2$ to form a chemical bond;

(b) hybridizing long sequence H of probe 1 and long sequence J of probe 2 to adjacent portions of the target sequence and hybridizing long sequence H' of probe 1' and long sequence J' of probe 2' to adjacent portions of the target complementary sequence;

(c) joining probe 1 and probe 2, hybridized after step (b) to adjacent portions of the target sequence, to each other by forming a chemical bond between chemical functionality groups $X_1$ and $Y_1$, thereby forming a first joined oligonucleotide product having the target complementary sequence;

(d) joining probe 1' and probe 2', hybridized after step (b) to adjacent portions of the target complementary sequence, to each other by forming a chemical bond between chemical functionality groups $X_2$ and $Y_2$, thereby forming a second joined oligonucleotide product having the target sequence;

(e) treating the sample under denaturing conditions;

(f) repeating steps (b) through (e) a desired number of times; and (g) detecting the joined oligonucleotide products.

DESCRIPTION OF THE DRAWINGS

FIG. 1 shows a generalized illustration of oligonucleotide probes 1, 1', 2 and 2'. The vertical lines in the illustration merely depict the demarcation between functionally distinct segments of each probe.

FIG. 2 shows adenine derivatives $A_1$, $A_2$, $A_3$ and $A_4$ modified with a chemical functionality group Z.

FIG. 3 shows cytidine derivatives $C_1$, $C_2$ and $C_3$ modified with a chemical functionality group Z.

FIG. 5 shows thymidine derivatives $T_1$, $T_2$, and $T_2$ modified with a chemical functionality group Z.

FIG. 7.1 shows a segment of two nucleotides from short sequences I' and K' of probes 1' and 2', respectively, with chemical functionality groups $X_2$ and $Y_2$ attached to guanine residues.

FIG. 15 shows the steps in the synthesis of protected 2'-amino-2'-deoxyguanosine phosphoramidite from 2'-amino-2'-deoxyguanine.

FIG. 16 shows the hybridization of the probes to the target sequence and joining of the probes via the chemical functionality groups to form a first joined oligonucleotide product.

FIG. 19 shows the hybridization of probes to the first and second joined oligonucleotide products from the first cycle of the amplification, and joining the probes to form more joined oligonucleotide products.

DETAILED DESCRIPTION OF THE INVENTION

Figure 4:
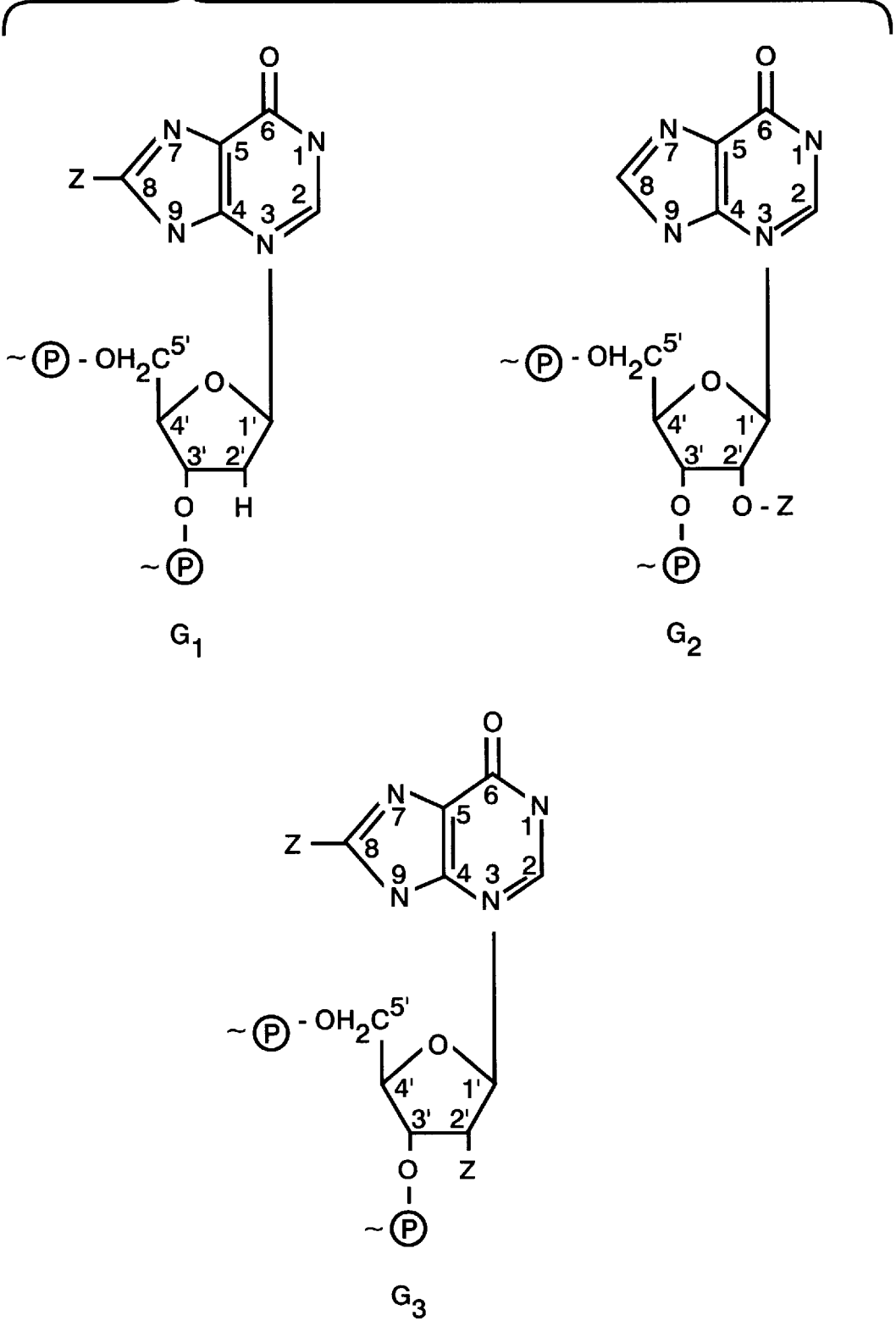
FIG. 4 shows guanine derivatives $G_1$, $G_2$ and $G_3$ modified with a chemical functionality group Z.
Figure 6:
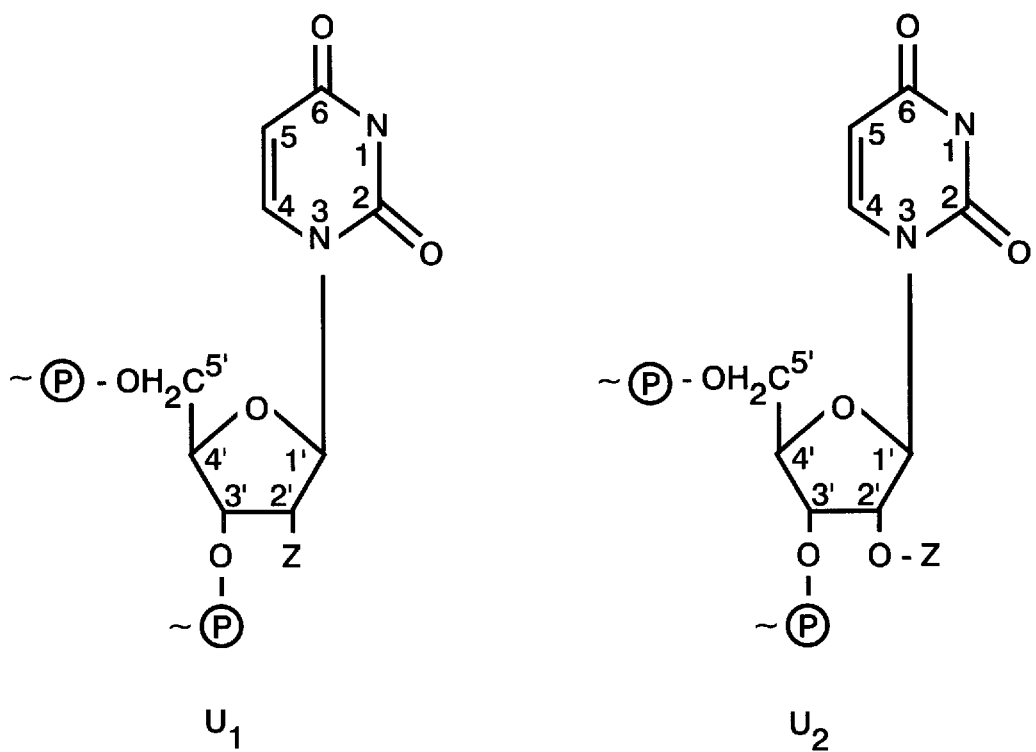
FIG. 6 shows uridine derivatives $U_1$ and $U_2$ modified with a chemical functionality group Z.

The present invention relates to a process for amplifying and detecting a target nucleic acid molecule in a test sample.

Target Nucleic Acid Molecule

The process of the present invention can produce geometric amplification of a target nucleic acid molecule, provided that at least part of the nucleotide sequence is known in sufficient detail that complementary oligonucleotide probe pairs can be synthesized. The target molecule can be in purified or non-purified form, and can be single stranded or double stranded DNA, RNA or a DNA-RNA hybrid.

The target nucleic acid molecule contains the specific nucleotide sequences that hybridize to the oligonucleotide probes. This sequence is called the target sequence. If a target nucleic acid molecule is double stranded, it will contain a target sequence and its complement called the target complementary sequence. The target sequence can be as short as twelve nucleotides, but preferably contains at least sixteen nucleotides and more preferably at least twenty nucleotides. There is no maximum number of nucleotides in the target sequence or target complementary sequence, which can constitute either a portion of the target molecule or the entire target molecule.

Any source of nucleic acid can be utilized as a source of the target nucleic acid molecule. For example, DNA or RNA isolated from bacteria, viruses, algae, protozoans, yeast, fungi, plasmids, cells in tissue culture and higher organisms such as plants or animals can be amplified with the process of the present invention.

DNA or RNA from these sources may, for example, be found in samples of a bodily fluid from an animal, including a human, such as, but not limited to, blood, urine, lymphatic fluid, synovial fluid, bile, phlegm, saliva, aqueous humor, lacrimal fluid, menstrual fluid and semen. In addition, samples containing DNA or RNA may, for example, be found in fluids from a plant, such as, but not limited to, xylem fluid, phloem fluid and plant exudates. Samples containing DNA or RNA may, for example, also be found in non-living sources such as, but not limited to, food, sewage, forensic samples, lakes, reservoirs, rivers and oceans.

Probes

The term "oligonucleotide complement pair" as used herein means two different oligonucleotide probes designated, for example, probe 1 and probe 1' or probe 2 and probe 2'. Probe 1 has a base sequence complementary to probe 1' and probe 2 has a base sequence complementary to probe 2'. Each pair of probes can be equal or unequal in length. It should be understood that more than two oligonucleotide complement pairs per target sequence or target complementary sequence could be used in the process of the present invention.

The term "oligonucleotide pair" as used herein refers to the grouping of probes 1 and 2 as a pair and the grouping of probes 1' and 2' as a pair.

Each probe has two distinct sequences. One sequence is generally longer than and the other. The two sequences will be referred to as the long sequence and the short sequence. The oligonucleotide probes are preferably constructed from deoxyribonucleotides, though ribonucleotides are acceptable substitutes.

Referring to the first oligonucleotide complement pair in FIG. 1, probe 1 has long sequence H and short sequence I. Probe 1' has long sequence H' and short sequence I'.

Referring to the second oligonucleotide complement pair in FIG. 1, probe 2 has long sequence J and short sequence K. Probe 2' has long sequence J' and short sequence K'.

Long sequence H of probe 1 and long sequence H' of probe 1' are complementary to each other. Long sequence J of probe 2 and long sequence J' of probe 2' are complementary to each other. Long sequence H is not complementary to long sequence J. Similarly, long sequence H' is not complementary to long sequence J'.

If a target nucleic acid sequence is present in a test sample, long sequences H and J are either entirely complementary or are sufficiently complementary to adjacent regions of the target sequence to form a stable hybrid under selected hybridization conditions.

If a strand complementary to a target nucleic acid sequence is present in a test sample, long sequences H' and J' are either entirely complementary to the target complementary sequence or are sufficiently complementary to adjacent regions of the target complementary sequence to form a stable hybrid under selected hybridization conditions.

The terms "adjacent regions of a target sequence" or "adjacent regions of a target complementary sequence" as used herein refer to sequences in these nucleic acid molecules that are either immediately abutting and juxtaposed to one another or are separated by one or two nucleotide bases.

The minimum number of nucleotides in the long sequence is the smallest number that gives sufficient selectivity in the amplification and detection process of the present invention. For example, a long sequence comprising at least six, preferably at least twelve and more preferably at least twenty deoxyribonucleotides or ribonucleotides is suitable.

The maximum length of the long sequence of a probe is limited only by the length of the target nucleic acid sequence in the test sample. The long sequence should be of sufficient length to form a stable hybrid with the target sequence, but is preferably not too long to require excessive hybridization times.

Some suitable maximum lengths of the long sequence are 200 nucleotides, preferably 150 nucleotides and more preferably 100 nucleotides.

Some suitable lengths of the long sequence are 6–100 nucleotides, preferably 10–70 nucleotides, more preferably 16–50 nucleotides and most preferably 18–30 nucleotides.

Short sequences I and K of probes 1 and 2, respectively, are complementary to each other. Short sequences I' and K' of probes 1' and 2', respectively, are complementary to each other.

Short sequences I and I' of probes 1 and 1', respectively, may or may not be complementary to each other. Similarly, short sequences K and K' of probes 2 and 2', respectively, may or may not be complementary to each other.

The short sequence of each probe is designed so that it does not hybridize to the target sequence when the long sequences of the probes have hybridized to the target sequence or to the target complementary sequence. Therefore, short sequence I hybridizes to short sequence K when long sequence H and long sequence J hybridize to adjacent portions of the target sequence. Likewise, short sequence I' hybridizes to short sequence K' when long sequence H' and long sequence J' hybridize to adjacent portions of the target complementary sequence.

The length of the short sequence is as short as possible to prevent hybridization between short sequences I and K when long sequences H and J are not hybridized to the target sequence or between short sequences I' and K' when long sequences H' and J' are not hybridized to the target complementary sequence.

The maximum length of the short sequence depends on the ratio of the long sequence to the short sequence. The ratio of the long sequence to the short sequence should be as large as possible, preferably in the range of 2:1 to 50:1. For example, the ratio should be at least 2:1, preferably at least 5:1, more preferably at least 10:1 and most preferably at least 20:1. For example, if the long sequence contains thirty nucleotides, the short sequence should contain at most ten nucleotides, preferably at most six nucleotides, more preferably at most three nucleotides and most preferably two nucleotides.

Each short sequence has a chemical functionality group, designated either X or Y, covalently attached to the sugar and/or base moieties of one or more of the nucleotides in the sequence. When the short sequences of probes 1 and 2 or probes 1' and 2' have hybridized to each other, the chemical functionality groups on each sequence chemically react to form a covalent bond that joins the probes together to form a joined oligonucleotide product. When the short sequences of probes 1 and 2 or probes 1' and 2' are not hybridized to each other, the nucleotide to which the chemical functionality group is attached and the neighboring nucleotide or nucleotides in the probe protect the chemical functionality group on the probe from reacting with the chemical functionality group on another probe.

Under the hybridization conditions used in the method, the long sequence must have a sufficiently high melting temperature to form a stable hybrid with a target sequence or target complementary sequence. The short sequence must have a sufficiently low melting temperature that it will not, under the same hybridization conditions, hybridize to the short complementary sequence of other probes unless the long probes have hybridized to the target sequence or target complementary sequence.

The term "melting temperature" as used herein refers to the temperature at which an oligonucleotide hybridizes to a complementary nucleic acid sequence to form a stable complex. The term is abbreviated "Tm." The Tm of a given oligonucleotide is a function of the size and composition of the oligonucleotide, the concentration of the oligonucleotide, and the composition of the reaction solvent.

The hybridization characteristics of the probes of the present invention are discussed herein in terms of the long and short lengths of the segments of the probes. Since the hybridization characteristics of a probe are largely determined by both the length and composition of the probe, it is understood that it is more accurate to characterize the long and short segments of the probes in terms of their respective melting temperatures. Accordingly, it is understood that the long sequence of a probe is the segment of the probe that has a higher melting temperature, with respect to its complementary sequence, than the short sequence of the probe, with respect to its complementary sequence. Similarly, it is understood that the short sequence of a probe is the segment of the probe that has a lower melting temperature, with respect to its complementary sequence, than the long sequence of the probe, with respect to its complementary sequence. Therefore, the more correct characterization of the two different segments of a probe is in terms of their respective melting temperatures. However, the general relationship between the length of a nucleotide sequence and the melting temperature of the sequence permits the different segments of the probes to be discussed in terms of their lengths as well as their melting temperatures.

The oligonucleotide probe pairs may be synthesized chemically from the four nucleotides in whole or in part by methods known in the art. Such methods include those described by Caruthers in Science 230, 281–285 (1985) and by Beaucage, et al., in Tetrahedron Letters 22, 1859–1862 (1981).

Chemical Functionality Groups

Chemical functionality groups X and Y (X=$X_1$ or $X_2$ and Y=$Y_1$ or $Y_2$) are pairs of atoms and/or groups that are reactive with each other to form covalent bonds when they are brought into close proximity with one another by hybridization of the short sequences of probes 1 and 2, respectively. It is understood that the distance of the chemical functionality groups should be approximately 4 Å or less in order for the reaction between the groups to occur.

A chemical functionality group is attached to the base or sugar moiety of at least one nucleotide in each short sequence. As seen in FIG. 1, chemical functionality group $X_1$ is attached to a nucleotide in short sequence I. As also seen in FIG. 1, chemical functionality group $X_2$ is attached to a nucleotide in short sequence I'. Similarly, chemical functionality group $Y_1$ is attached to a nucleotide in short sequence K and chemical functionality group $Y_2$ is attached to a nucleotide in short sequence K'.

Chemical functionality groups $X_1$ and $X_2$ can be the same or different and chemical functionality groups $Y_1$ and $Y_2$ can be the same or different as long as $X_1$ can form a covalent bond with $Y_1$ and $X_2$ can form a covalent bond with $Y_2$ when short sequences I and K and I' and K' are hybridized to each other, respectively.

A chemical functionality group is covalently attached to a nucleotide in the short sequence at a sterically tolerant site. A sterically tolerant site is defined as a position on a nucleotide base or sugar moiety at which the chemical functionality group can be attached without causing significant interference with hybridization of the short sequences to each other or hybridization of the long sequences to the target sequence or to the target complementary sequence. Sterically tolerant sites include positions on the purine and pyrimidine bases and polyvalent heteroatoms of the base or ribose portion of the nucleotides or modified nucleotides.

Examples of sterically tolerant sites include the methyl group attached to the C-5 position of thymidine, the amino group attached to the C-6 position of adenine or cytidine, the C-8 position of adenine or guanine, the C-2' position of the ribose ring of each type of nucleotide and the hydroxyl group attached to the C-2' position of the ribose ring of a ribonucleotide.

The modification of the purine and pyrimidine bases may, for example, be performed according to methods known in the art, such as those described by Ruth in EP 135 587. The modification of a ribonucleotide at the C-2' position of the ribose ring of the ribonucleotide may, for example, be performed according to the method described by Yamana, K. et al. in *Bioconjugate Chemistry* 1, 319–324 (1990).

An example of nucleotides modified with a chemical functionality group at each of the above-mentioned sterically tolerant sites is shown in FIGS. 2–6. Where modified deoxyribonucleotides are shown in FIGS. 2–6, it is understood that ribonucleotides are acceptable substitutes. A list of the designations of the modified nucleotides is provided below.

$A_1$ represents adenine with a chemical functionality group Z replacing a hydrogen from the amino group located at the C-6 position $A_2$ represents adenine with a chemical functionality group Z attached to the hydroxyl group located at the C-2' position of the ribose ring $A_3$ represents adenine with chemical functionality group Z replacing the hydrogen located at the C-8 position $A_4$ represents adenine with chemical functionality group Z replacing the hydroxyl group located at the C-2' position of the ribose ring $C_1$ represents cytidine with a chemical functionality group Z replacing a hydrogen from the amino group located at the C-6 position $C_2$ represents cytidine with a chemical functionality group Z attached to the hydroxyl group located at the C-2' position of the ribose ring $C_3$ represents cytidine with chemical functionality group Z replacing the hydroxyl group located at the C-2' position of the ribose ring $G_1$ represents guanine with chemical functionality group Z replacing the hydrogen located at the C-8 position $G_2$ represents guanine with a chemical functionality group Z attached to the hydroxyl group located at the C-2' position of the ribose ring $G_3$ represents guanine with chemical functionality group Z replacing the hydroxyl group located at the C-2' position of the ribose ring $T_1$ represents thymidine with chemical functionality group Z replacing a hydrogen from the methyl group located at the C-5 position $T_2$ represents thymidine with a chemical functionality group Z attached to the hydroxyl group located at the C-2' position of the ribose ring $T_3$ represents thymidine with chemical functionality group Z replacing the hydroxyl group located at the C-2' position of the ribose ring $U_1$ represents uridine with chemical functionality group Z replacing the hydroxyl group located at the C-2' position of the ribose ring $U_2$ represents uridine with a chemical functionality group Z attached to the hydroxyl group located at the C-2' position of the ribose ring Z represents chemical functionality groups $X_1$, $X_2$, $Y_1$, or $Y_2$ It is apparent that a fairly large number of terms have been defined above, in order to describe the various sequences, modified nucleotides and chemical functionality groups used in the present invention. Some additional terms are defined below. For the convenience of the reader, a Glossary is given at the end of the Examples section below where all of these terms are collected in one place.

It is important to note that chemical functionality groups X and Y do not have to be attached to the same positions on their respective nucleotides. For example, without limitation, group X could be attached to position C-2' on a nucleotide of the short sequence of probe 1 and group Y could be attached to position C-6 on an appropriate nucleotide of the short sequence of probe 2.

The position to which the chemical functionality groups are attached to a nucleotide in the short sequence of a probe may determine the minimum length of the short sequence. For example, when chemical functionality groups are attached to the C-2' position of a nucleotide in the short sequence of both members of an oligonucleotide pair, the short sequences may be as short as 2–3 nucleotides. However, when one member of an oligonucleotide pair has a chemical functionality group attached to the C-2' position of a nucleotide in its short sequence and the other member of the pair has a chemical functionality group attached to a position other than the C-2' position of a nucleotide in its short sequence, the short sequences may be as short as 1–3 nucleotides. Similarly, when neither member of an oligonucleotide pair has a chemical functionality group attached to the C-2' position of a nucleotide in its short sequence, the short sequence may be as short as 1–3 nucleotides.

The preferred position for attaching the chemical functionality groups to a nucleotide is the C-2' position of the ribose ring of the nucleotide. For example, it is convenient to replace the hydroxyl group at the C-2' position of the ribose ring with an amino group by, for example, the protocol described in Moffatt, et al., *J. Org. Chem.* 36, 250 (1971) and Ruth in EP 135 587. The amino group can serve either as a chemical functionality group, or as a bridging group for the attachment of chemical functionality groups to the ribose ring.

Chemical functionality groups can optionally contain a bridging group through which it is attached to the nucleotide. Examples of bridging groups include, but are not limited to, amino, amido, thio, carbonyl, carboxyl, alkyl groups, aryl groups alkylaryl groups, arylalkyl groups optionally substituted at any position with groups such as amido, carbonyl, carboxyl, amino and thio. Alkyl groups may be cyclic in whole or in part. Examples of alkyl groups include, but are not limited to, methyl, ethyl, propyl, butyl, pentyl, cyclopentyl, hexyl, cyclohexyl, etc. Examples of aryl groups include, but are not limited to, phenyl, naphthyl, imidazolyl, indyl, etc. In addition, for purposes of illustration, the term "Ph" as used herein refers to a phenyl group. A phenyl group substituted at, for example, positions 1 and 3 is denoted 1,3 Ph.

Some specific examples of chemical reactions suitable for the present method are shown below. In these examples, D represents modified nucleotides $A_4$, $C_3$, $G_3$, $T_3$ or $U_1$; E represents modified nucleotides $A_1$ or $C_1$; F represents modified nucleotides $A_3$ or $G_1$; and L represents modified ribonucleotides $A_2$, $C_2$, $G_2$, $T_2$ and $U_2$ depicted in FIGS. 2–6 (See also "Glossary" below at the end of the Examples section).

In a given pair of complementary short sequences, for example, one member of the pair has a nucleophilic chemical functionality group and the other member of the pair has an electrophilic chemical functionality group (i.e. if X in FIG. 1 is a nucleophile, then Y is an electrophile, and visa versa).

Some examples of nucleophiles include —SH, —NH$_2$, —NHA (where A is an alkyl group, such as methyl, ethyl, propyl, butyl, etc., or an aryl group, such as phenyl, naphthyl, imidazolyl, indyl, etc.). Electrophiles are capable of forming single or double bonds via electron transfer from a nucleophile. The reaction between the nucleophile and the electrophile may involve the addition of the nucleophile across a double bond attached to an electron withdrawing group or the substitution of a nucleophile for an electrophilic leaving group.

Examples of the addition of a nucleophile across a double bond involving the addition of a thiol group to the double bond of a maleimido moiety are shown below. The general scheme of the reaction is as follows, wherein R-Z and R'-Z represent any of the modified nucleotides shown in FIGS. 2–6:

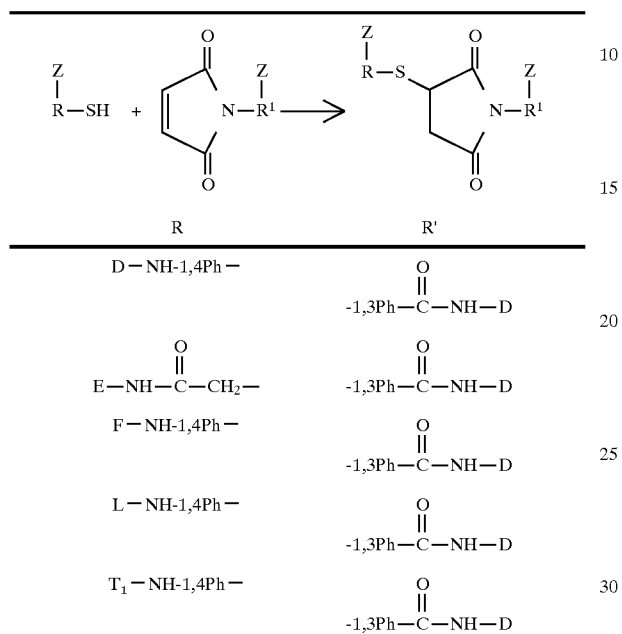

| R | R' |
|---|---|
| D—NH-1,4Ph— | $\underset{\text{-1,3Ph—C—NH—D}}{\overset{O}{\underset{\|}{\|}}}$ |
| E—NH—C(=O)—CH$_2$— | -1,3Ph—C(=O)—NH—D |
| F—NH-1,4Ph— | -1,3Ph—C(=O)—NH—D |
| L—NH-1,4Ph— | -1,3Ph—C(=O)—NH—D |
| T$_1$—NH-1,4Ph— | -1,3Ph—C(=O)—NH—D |

The general scheme of the Michael reaction is as follows:

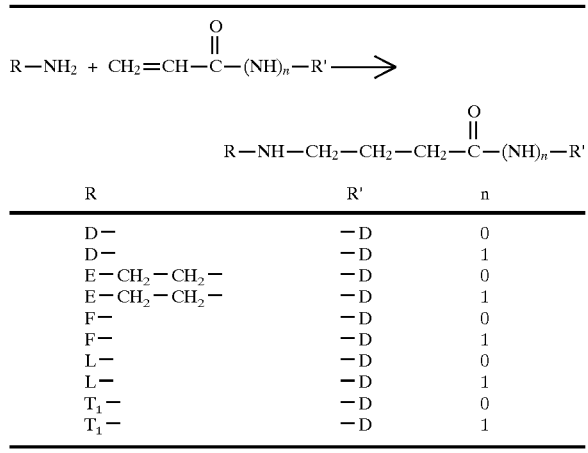

| R | R' | n |
|---|---|---|
| D— | —D | 0 |
| D— | —D | 1 |
| E—CH$_2$—CH$_2$— | —D | 0 |
| E—CH$_2$—CH$_2$— | —D | 1 |
| F— | —D | 0 |
| F— | —D | 1 |
| L— | —D | 0 |
| L— | —D | 1 |
| T$_1$— | —D | 0 |
| T$_1$— | —D | 1 |

The general scheme of a reaction involving the substitution of a nucleophile for an electrophilic leaving group is as follows:

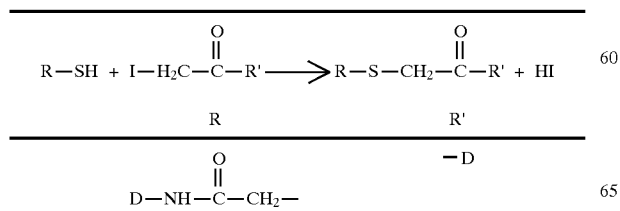

| R | R' |
|---|---|
| D—NH—C(=O)—CH$_2$— | —D |
| E—NH—C(=O)—CH$_2$— | —D |
| F—NH—C(=O)—CH$_2$— | —D |
| L—NH—C(=O)—CH$_2$— | —D |
| T$_1$—NH—C(=O)—CH$_2$— | —D |
| D—NH—C(=O)—S-1,4Ph— | —D |
| E—NH—C(=O)—S-1,4Ph— | —D |
| F—NH—C(=O)—S-1,4Ph— | —D |
| L—NH—C(=O)—S-1,4Ph— | —D |
| T$_1$—NH—C(=O)—S-1,4Ph— | —D |

Other types of reactions between the chemical functionality groups are, for example, the Diels-Alder reaction or any pericyclic reaction that produces one or more new covalent bonds. The general scheme of the Diels-Alder reaction is as follows:

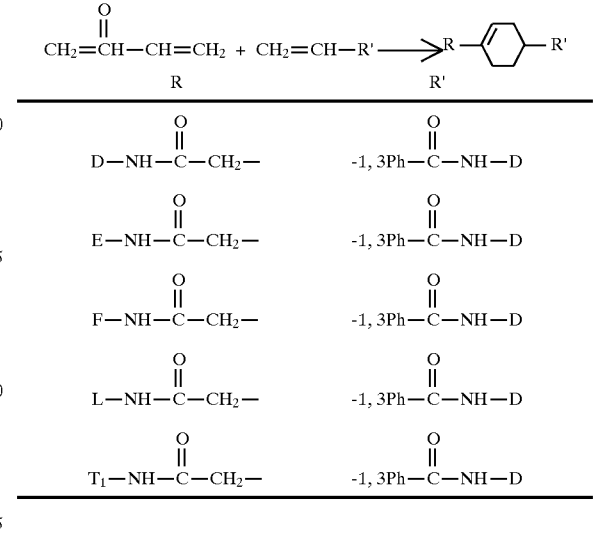

| R | R' |
|---|---|
| D—NH—C(=O)—CH$_2$— | -1,3Ph—C(=O)—NH—D |
| E—NH—C(=O)—CH$_2$— | -1,3Ph—C(=O)—NH—D |
| F—NH—C(=O)—CH$_2$— | -1,3Ph—C(=O)—NH—D |
| L—NH—C(=O)—CH$_2$— | -1,3Ph—C(=O)—NH—D |
| T$_1$—NH—C(=O)—CH$_2$— | -1,3Ph—C(=O)—NH—D |

Further examples of Diels-Alder reactions between chemical functionality groups are as follows:

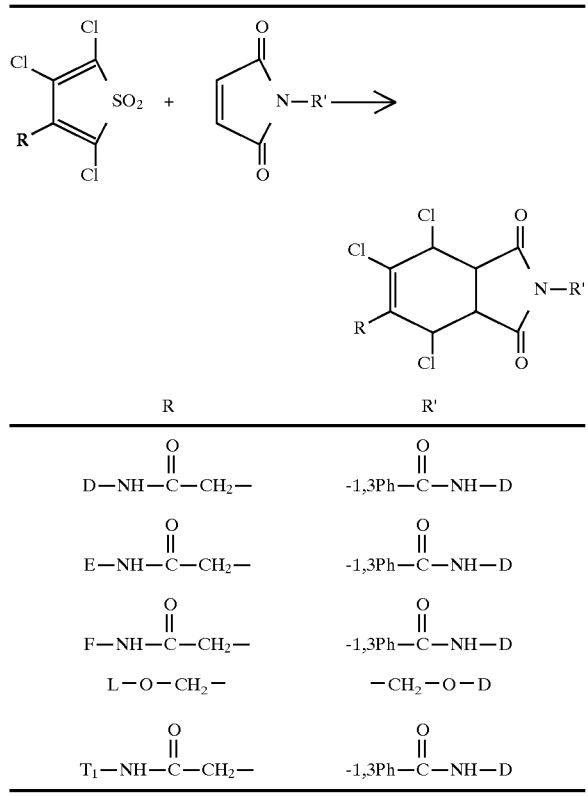

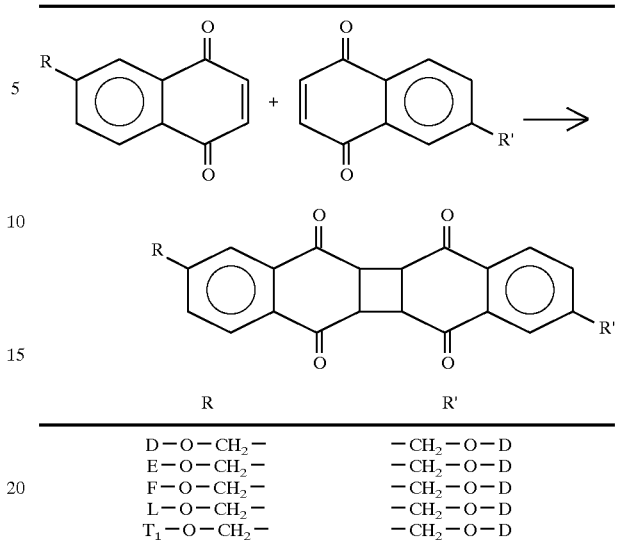

Chemical functionality groups can also be selected that form covalent bonds via a photochemical reaction such as [2+2] photocyclodimerization or other type of photocycling. An example of a [2+2] photo-cyclodimerization reaction is shown below.

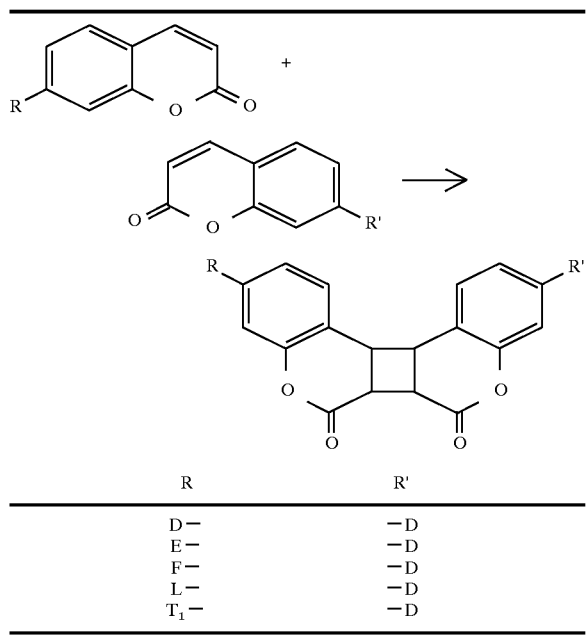

Further examples of a [2+2] photo-cyclodimerization reaction between chemical functionality groups are shown below. The general scheme of the reaction is as follows:

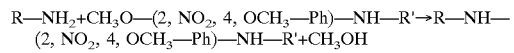

Another example of a photochemical reaction between chemical functionality groups is shown below, wherein a phenyl group is substituted at the 2 position with a $NO_2$ group and at the 4 position with an $OCH_3$ group. The substituted phenyl group is designated (2, $NO_2$, 4, $OCH_3$—Ph). R and R' represent any naturally occurring deoxyribonucleotide or ribonucleotide.

R—$NH_2$+$CH_3$O—(2, $NO_2$, 4, $OCH_3$—Ph)—NH—R'→R—NH—(2, $NO_2$, 4, $OCH_3$—Ph)—NH—R'+$CH_3$OH

Description of the Chemical Amplification and Detection Process

Amplification of a target nucleic acid sequence is accomplished in the present invention by joining two or more chemically modified oligonucleotide probes for each strand of a target nucleic acid molecule to form a joined oligonucleotide product. Once formed, the joined oligonucleotide product serves as a template for further production of joined oligonucleotide products. The steps of the process are repeated a sufficient number of times to produce detectable amounts of joined oligonucleotide product. Each repetition of the steps of the process of the present invention is referred to as a cycle. The number of cycles needed to produce detectable amounts of joined oligonucleotide produce depends in large part on the number of target molecules initially present in a sample. The greater the number of target molecules in a sample, the fewer the number of cycles needed to produce detectable amounts of joined oligonucleotide product. When a desired amount of joined oligonucleotide product is formed, it is detected. A novel aspect of the present invention is the way in which the oligonucleotide probes form the joined oligonucleotide product. Neither DNA polymerase nor DNA ligase is used in the present invention to form the joined oligonucleotide product.

Probes 1, 1', 2, and 2' are used in the process of the present invention as follows to amplify target sequences in a single or double stranded nucleic acid molecule.

As described above, when a target sequence is present in a test sample, under carefully controlled hybridization conditions, only long sequences H and J of oligonucleotide probes 1 and 2, respectively, hybridize to adjacent regions of the target sequence. This leaves short sequences I and K of probes 1 and 2, respectively, unhybridized to the target sequence. When long sequences H and J have formed stable hybrid complexes with the target sequence, short sequences I and K are forced into proximity with each other and, since they are complementary, hybridize to each other. When sequences I and K are hybridized to each other, chemical functionality groups $X_1$ and $Y_1$ are brought into sufficiently close proximity to form a covalent bond. The bond between chemical functionality groups $X_1$ and $Y_1$ joins probe 1 to probe 2, forming a first joined oligonucleotide product. Once formed, the two sequences of the first joined oligonucleotide product constitute a "target complementary sequence," and are complementary to adjacent sequences of the target sequence.

Similarly, when long sequences H' and J' of probes 1' and 2', respectively, hybridize to adjacent regions of the target complementary sequence, short sequences I' and K' of probes 1' and 2', respectively, hybridize to each other. The hybridization of short sequences I' and K' bring chemical functionality group $X_2$ of sequence I' and chemical functionality group $Y_2$ of sequence K' into sufficient proximity to form a covalent bond that joins probes 1' and 2' together to produce a second joined oligonucleotide product. Once formed, the two sequences of the second joined oligonucleotide product constitute a "target sequence" and are complementary to adjacent sequences of the target complementary sequence.

Figure 9:
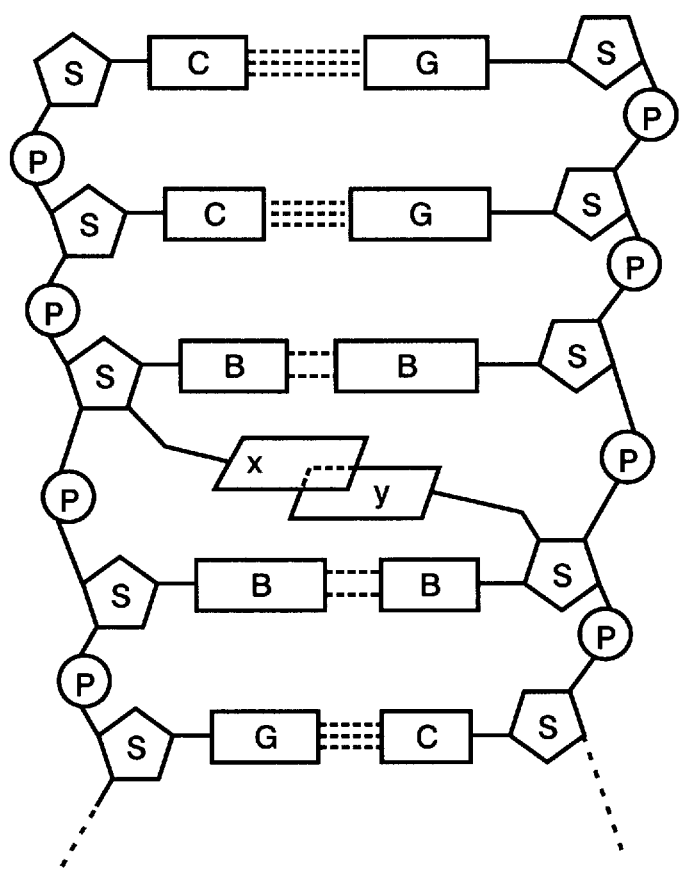
FIG. 9 shows a generalized illustration of two hybridized short sequences with chemical functionality groups X and Y attached to the C-2' position of the ribose ring of both nucleotide bases B. In the Figure, X and Y each represent a chemical functionality group, G represents guanine, C represents cytosine, B represents any nucleotide base and the string of symbols with S or P inside represents the sugar-phosphate backbone of the nucleic acid sequence. The nucleotide bases to which the chemical functionality groups are attached are not hybridized to each other. Instead, chemical functionality group X is attached to the nucleotide that hybridizes to the nucleotide adjacent to the nucleotide to which chemical functionality group Y is attached. Chemical functionality groups X and Y are understood to be joined together with a covalent bond.

The chemical functionality groups on each probe are protected and sheltered by nucleotides of the short sequences to which the groups are attached and their neighboring nucleotides from access by chemical functionality groups on other probes when the short sequence of a probe is not hybridized to the short sequence of another probe. A generalized illustration of a protected chemical functionality group attached to a short sequence is shown in FIG. 9.

As a result of the protection of the chemical functionality group by the nucleotides of the short sequence, each chemical functionality group is prevented from reacting with the chemical functionality groups on other probes unless the chemical functionality groups are brought into sufficiently close proximity by the hybridization of the short sequences to each other.

Generalized illustrations of two hybridized short sequences with chemical functionality groups attached to the nucleotide bases depicted in FIGS. 2–6 are shown in FIGS. 10–14. It is understood that in FIGS. 10–14, chemical functionality groups X and Y are joined together by covalent bonds.

Figure 10:
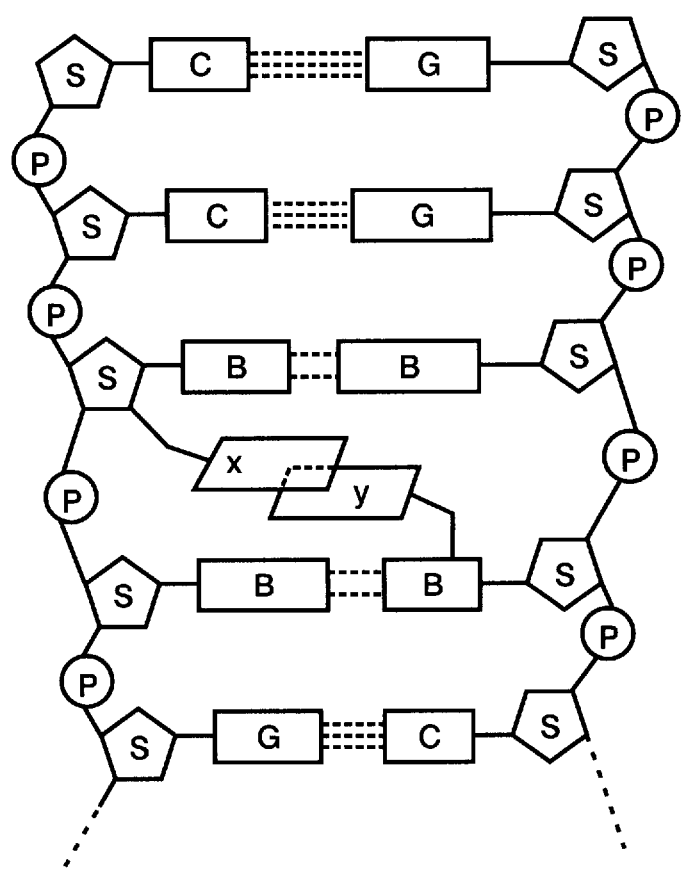
FIG. 10 shows a generalized illustration of two hybridized short sequences with chemical functionality group X attached to the C-2' position of the ribose ring of a nucleotide base B and chemical functionality group Y attached to either the C-5, C-6 or C-8 positions of a nucleotide base B. In the Figure, X and Y each represent a chemical functionality group, G represents guanine, C represents cytosine, B represents any nucleotide base and the string of symbols with S or P inside represents the sugar-phosphate backbone of the nucleic acid sequence. The nucleotide bases to which the chemical functionality groups are attached are not hybridized to each other. Chemical functionality groups X and Y are understood to be joined together with a covalent bond.

As can be seen in FIG. 10, chemical functionality groups X and Y can be attached to the C-2' position of the ribose ring of each nucleotide B. The nucleotide bases to which the chemical functionality groups are attached are not hybridized to each other. Instead, chemical functionality group X is attached to the nucleotide that hybridizes to the nucleotide adjacent to the nucleotide to which chemical functionality group Y is attached.

Figure 11:
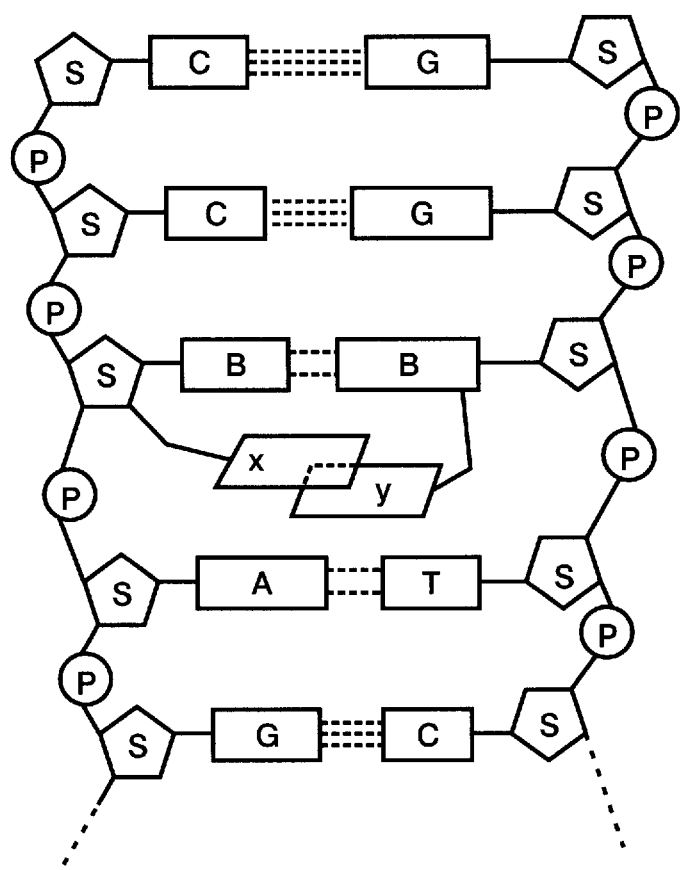
FIG. 11 shows a generalized illustration of two hybridized short sequences with chemical functionality group X attached to the C-2' position of the ribose ring of a nucleotide base B and chemical functionality group Y attached to either the C-5, C-6 or C-8 positions of a nucleotide base B. In the Figure, X and Y each represent a chemical functionality group, G represents guanine, C represents cytosine, A represents adenine, T represents thymidine, B represents any nucleotide base and the string of symbols with S or P inside represents the sugar-phosphate backbone of the nucleic acid sequence. The nucleotide bases to which the chemical functionality groups are attached are hybridized to each other. Chemical functionality groups X and Y are understood to be joined together with a covalent bond.

As can be seen in FIG. 11, chemical functionality group X can be attached to the C-2' position of the ribose ring of a nucleotide base B and chemical functionality group Y can be attached to either the C-5, C-6 or C-8 positions of a nucleotide base B. In the embodiment shown in FIG. 11, the nucleotide bases to which the chemical functionality groups are attached are not hybridized to each other.

Figure 12:
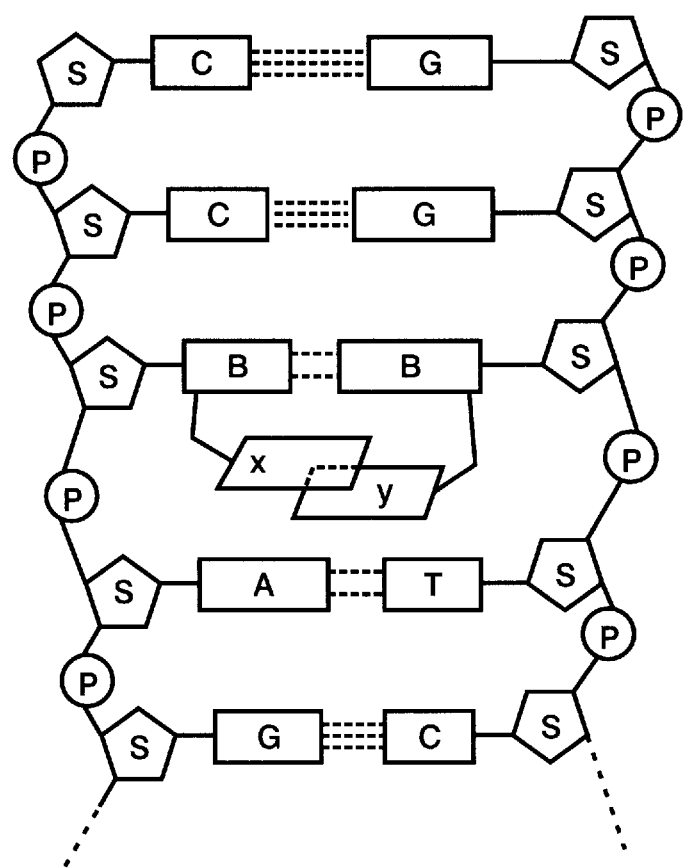
FIG. 12 shows a generalized illustration of two hybridized short sequences with chemical functionality group X attached to either the C-5, C-6 or C-8 positions of a nucleotide base B and chemical functionality group Y attached to either the C-5, C-6 or C-8 positions of a nucleotide base B. In the Figure, X and Y each represent a chemical functionality group, G represents guanine, C represents cytosine, A represents adenine, T represents thymidine, B represents any nucleotide base and the string of symbols with S or P inside represents the sugar-phosphate backbone of the nucleic acid sequence. The nucleotide bases to which the chemical functionality groups are attached are hybridized to each other. Chemical functionality groups X and Y are understood to be joined together with a covalent bond.

As can be seen in FIG. 12, chemical functionality group X can be attached to the C-2' position of the ribose ring of a nucleotide base B and chemical functionality group Y can be attached to either the C-5, C-6 or C-8 positions of a nucleotide base B. In the embodiment shown in FIG. 12, the nucleotide bases to which the chemical functionality groups are attached are hybridized to each other.

Figure 13:
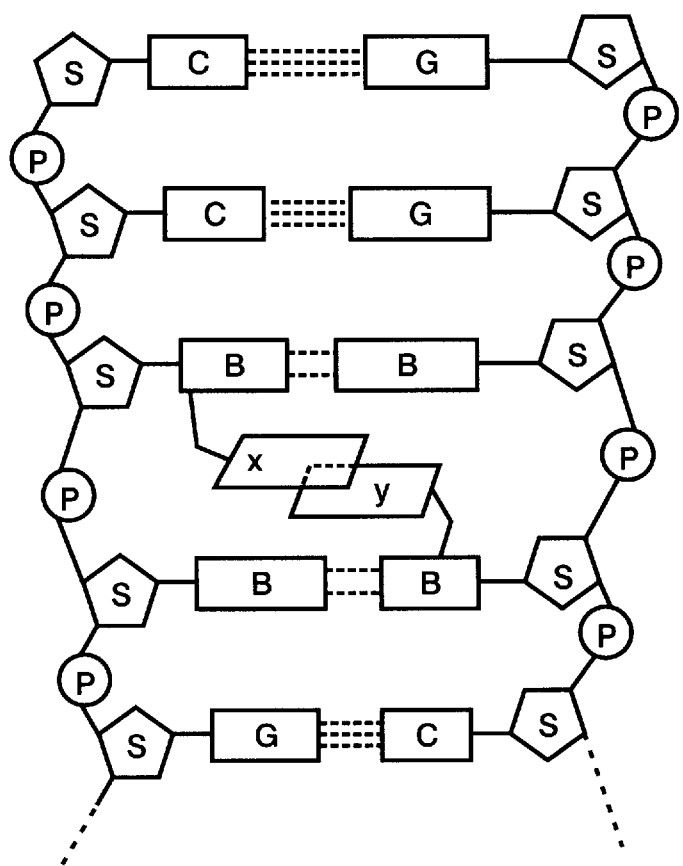
FIG. 13 shows a generalized illustration of two hybridized short sequences with chemical functionality group X attached to either the C-5, C-6 or C-8 positions of a nucleotide base B and chemical functionality group Y attached to either the C-5, C-6 or C-8 positions of a nucleotide base B. In the Figure, X and Y each represent a chemical functionality group, G represents guanine, C represents cytosine, B represents any nucleotide base and the string of symbols with S or P inside represents the sugar-phosphate backbone of the nucleic acid sequence. The nucleotide bases to which the chemical functionality groups are attached are not hybridized to each other. Chemical functionality groups X and Y are understood to be joined together with a covalent bond.

As can be seen in FIG. 13, chemical functionality group X can be attached to either the C-5, C-6 or C-8 positions of a nucleotide base B and chemical functionality group Y can be attached to either the C-5, C-6 or C-8 positions of a nucleotide base B. In the embodiment shown in FIG. 13, the nucleotide bases to which the chemical functionality groups are attached are hybridized to each other.

Figure 14:
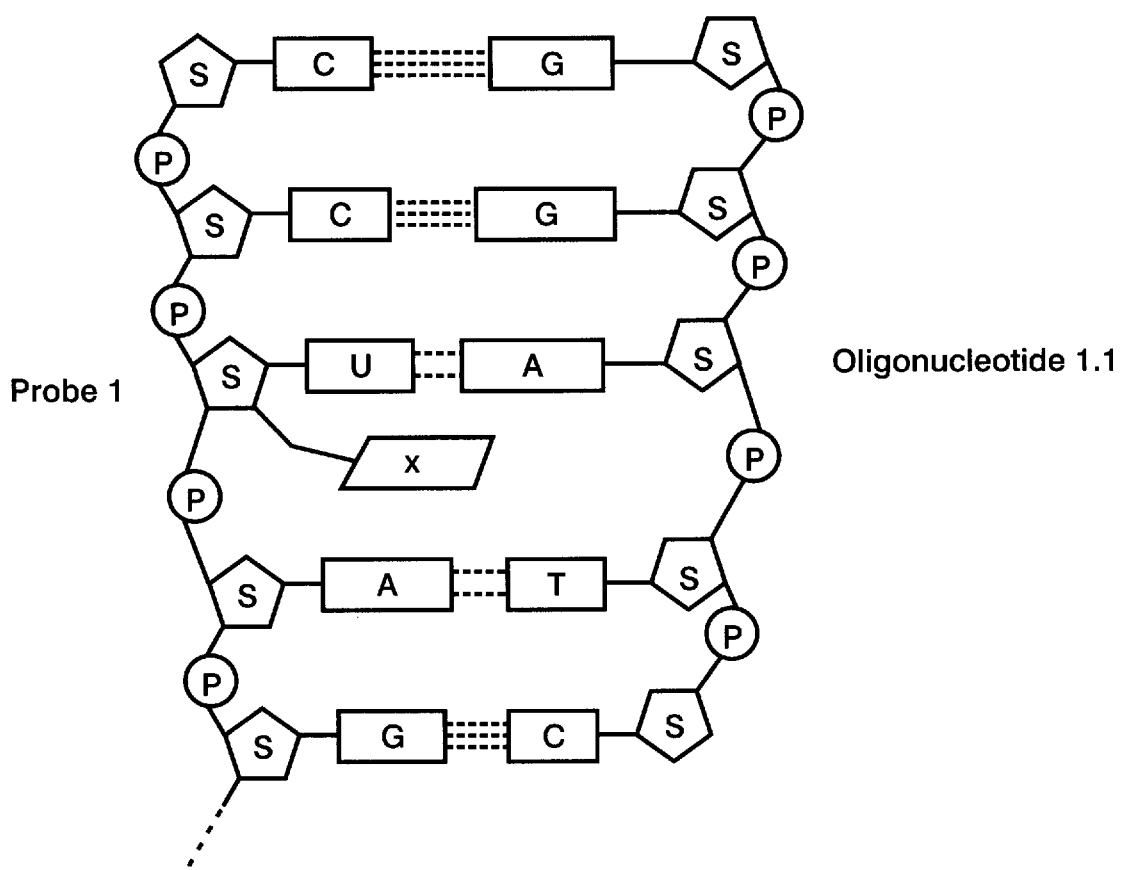
FIG. 14 shows a generalized illustration of a chemical functionality group X protected with oligonucleotide 1.1.

As can be seen in FIG. 14, chemical functionality group X can be attached to either the C-5, C-6 or C-8 positions of a nucleotide base B and chemical functionality group Y can be attached to either the C-5, C-6 or C-8 positions of a nucleotide base B. In the embodiment shown in FIG. 14, the nucleotide bases to which the chemical functionality groups are attached are not hybridized to each other.

A generalized illustration of both pairs of oligonucleotide probes hybridized to a double stranded target molecule and joined by chemical functionality groups to form a first and a second joined oligonucleotide product is shown below. It is understood that in the preferred embodiments of the present invention, there is no gap between the probes, although a gap of one or two nucleotides is permissible.

Target sequence

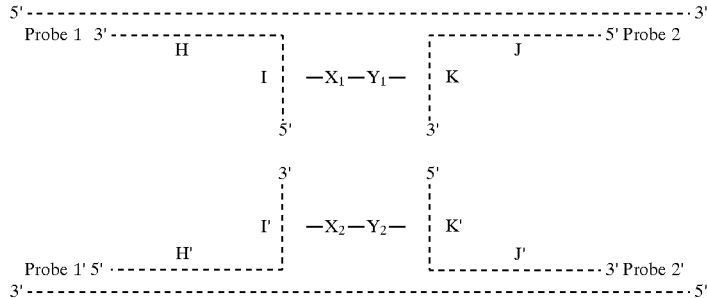

Target complementary sequence

In a sample containing a single stranded target molecule, the second joined oligonucleotide product is formed after the first cycle. In order to form a second joined oligonucleotide product in the absence of a target complementary molecule, a first joined oligonucleotide product must be formed in the first cycle of the process. The first joined oligonucleotide product has the target complementary sequence and functions as a template to which probes 1' and 2' hybridize. Probes 1' and 2' form a second joined oligonucleotide product having the target sequence in the second cycle and subsequent cycles of the process.

Once the first joined oligonucleotide product is formed in the first cycle of the process, the product is separated from the target sequence by denaturation. The terms "denature" or "denaturation" as used herein means the reversible loss of higher order structure and separation of hybridized nucleic acids into single strands, produced by physiological or non-physiological conditions, such as, for example, enzymes, pH, temperature, salt or organic solvents.

The second joined oligonucleotide product is also separated from the target complementary sequence or first joined oligonucleotide product by denaturation once it is formed. The target molecule and the first and second joined oligonucleotide products serve as templates for repeated cycles of the process.

A generalized illustration of the first cycle of the amplification process of the present invention for a single stranded sequence is shown in FIG. 16.

Figure 17:
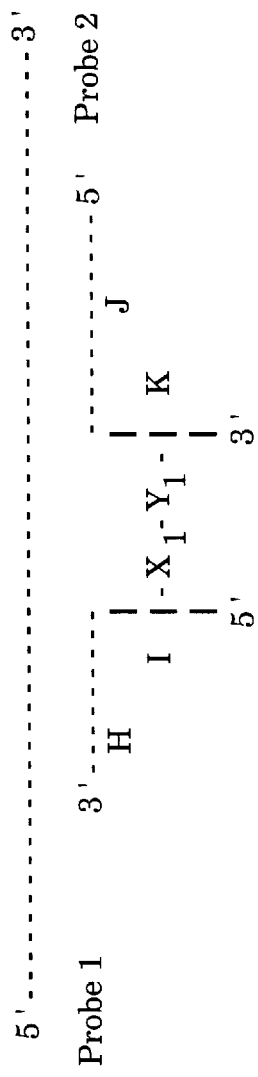
FIG. 17 shows the hybridization of the probes to the target sequence and the target complementary sequence and joining of the probes via the chemical functionality groups to form joined oligonucleotide products.
Figure 18:
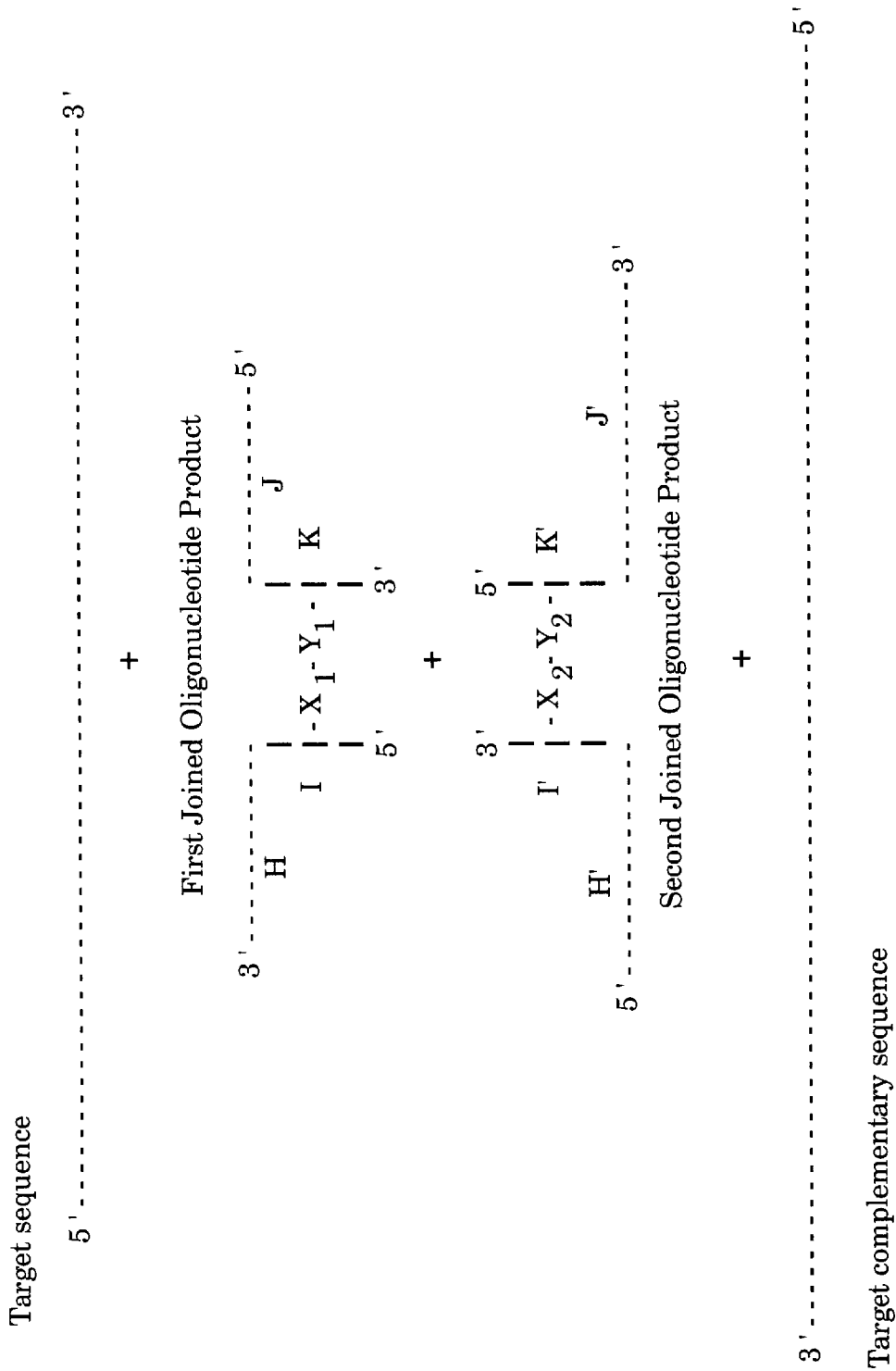
FIG. 18 shows the denaturation of the first and second joined oligonucleotide products from the target sequence and the target complementary sequence, respectively.

A generalized illustration of the first cycle of the amplification process for a double stranded sequence is shown in FIGS. 17 and 18.

Once the first cycle of the process is completed, further amplification of the target sequence is achieved by repeated cycles of denaturation of the joined oligonucleotide products, annealing of the probe pairs to the joined oligonucleotide products and formation of covalent bonds between the chemical functionality groups on the short sequences to produce more joined oligonucleotide products. All cycles after the first cycle necessarily have both target sequence (single and double stranded target molecules and second joined oligonucleotide product) and target complementary sequence (double stranded target molecule and first oligonucleotide product).

A generalized illustration of the ability of the first and second joined oligonucleotide products to act as templates for the formation of additional first and second joined oligonucleotide products during the second and all subsequent cycles of the amplification process for a single and double stranded target sequence is shown in FIG. 19.

Target-independent hybridization of the short sequences is avoided by maintaining a reaction temperature sufficiently below the melting temperature (Tm) of the long sequences (H, H', J and J') to permit stable hybridization of the long sequences to the target sequence or the target complementary sequence, but above the Tm of the short sequences (I, I', K, and K') to prevent the short sequences from stably hybridizing to one another when the probes are not fully hybridized to the target sequence or the target complementary sequence. Under such stringency conditions, complementary short sequences (I and K; I' and K') hybridize to each other only when the long sequences of the probes have hybridized to adjacent portions of the target sequence or the target complementary sequence. The short sequences can then form sufficiently stable hybrids to permit the chemical functionality groups to react and form joined oligonucleotide product. Accordingly, the length of the short sequences must be chosen so that, under the reaction conditions used, their Tm's are sufficiently low to avoid target-independent hybridization of the short sequences while the length of the long sequences must be chosen so they can efficiently form stable hybrids with the target sequence or the target complementary sequence.

In another embodiment of the present invention, linear amplification of a target sequence or a target complementary sequence, if present, can be accomplished by using only probes 1 and 2 or probes 1' and 2' in the above-described process.

In a preferred embodiment of the present invention, a standard hybridization buffer, such as, for example, 30% deionized formamide in water (vol/vol), 0.54M NaCl, 0.03M sodium phosphate (pH 7.4), 0.003M EDTA, 5% dextran sulfate 500K m.w. (Sigma)(w/vol) and 0.1% Triton X-100, is used with oligonucleotides of any length from six to one hundred nucleotides. Only the temperature of denaturation and the temperature of hybridization change as the length (more accurately, the Tm) of the oligonucleotide probes change. The hybridization temperature and the denaturation temperature are both functions of the length of the oligonucleotide probes. The following table shows a preferred average relationship of the length of the oligonucleotide probes to the hybridization and denaturation temperatures.

| Length of Probes | Hybridization Temperature | Denaturation Temperature |
| --- | --- | --- |
| 6 nucleotides | 20° C. | 40° C. |
| 12 nucleotides | 30° C. | 60° C. |
| 16 nucleotides | 45° C. | 64° C. |
| 24 nucleotides | 55° C. | 85° C. |
| 32 nucleotides | 65° C. | 90° C. |

Generally, the oligonucleotide pairs will be present in molar excess of about $10^5$–$10^{15}$, preferably $10^9$–$10^{15}$, pairs per nucleic acid target sequence or target complementary sequence. The exact amount of the pairs to be used in diagnostic purposes may not be known due to uncertainty as to the amount of the nucleic acid target in a sample. However, using an average amount of $10^{15}$ oligonucleotide pairs is applicable in a typical diagnosis assay format. A large molar excess is preferred in any case to improve the efficiency of the process of the invention.

Since the chemical functionality groups are prohibited from reacting and joining the probes together if the long sequences of both probes have not hybridized to the target sequence and the short sequences of the probes have not hybridized to each other formation of target-independent joined oligonucleotide product is avoided.

Once a sufficient quantity of joined oligonucleotide products are produced, they are detected by routine methods in the art, such as, for example by immobilizing one member of a joined oligonucleotide product (i.e. 1 or 1') and labeling the other member (i.e. 2 or 2') with, for example, one or more radioactive, chromogenic, chemiluminescent, or fluorescent signals, or by sizing the joined oligonucleotide products on a gel.

Methods for labelling oligonucleotide probes have been described, for example, by Leary et al., Proc. Natl. Acad. Sci. USA (1983) 80:4045; Renz and Kurz, Nucl. Acids Res. (1984) 12:3435; Richardson and Gumport, Nucl. Acids Res. (1983) 11:6167; Smith et al., Nucl. Acids Res. (1985) 13:2399; and Meinkoth and Wahl, Anal. Biochem. (1984) 138:267.

The label may be radioactive. Some examples of useful radioactive labels include $^{32}P$, $^{125}I$, $^{131}I$, and $^{3}H$. Use of radioactive labels have been described in U.K. 2,034,323, U.S. Pat. Nos. 4,358,535, and 4,302,204.

Some examples of non-radioactive labels include enzymes, chromophors, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels have been described in U.K. 2,019,404, EP 63,879, and by Rotman, Proc. Natl. Acad. Sci., 47, 1981–1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

Detection of the joined oligonucleotide product is performed by methods known in the art, such as with a radioactive label or with a non-radioactive capture assay. For example, joined oligonucleotide products with a radioactive label are detected by autoradiography following sizing of the joined oligonucleotide products on a gel. Alternatively, joined oligonucleotide products are detected in a non-radioactive capture assay by attaching a receptor, such as, for example, biotin to probe 1 and attaching an enzymatic label, such as, for example, alkaline phosphatase, to probe 2. A microtiter plate coated with a ligand for the receptor, such as, for example, avidin is used to capture probe 1 via the biotin attached to the probe. The enzymatic label attached to probe 2 is exposed to a chromogenic substrate, such as 5-bromo-4-chloro-3-indolyl phosphate/nitro blue tetrazolium, for example, and a colorimetric change in the substrate is detected by measuring the optical density (O.D.) of the solution.

The labels may be conjugated to the antibody or nucleotide probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate.

Alternatively, labels such as enzymes and chromophoric molecules may be conjugated to the antibodies or nucleotides by means of coupling agents, such as dialdehydes, carbodiimides, dimaleimides, and the like.

The label may also be conjugated to the probe by means of a ligand attached to the probe by a method described above and a receptor for that ligand attached to the label. Any of the known ligand-receptor combinations is suitable. Some suitable ligand-receptor pairs include, for example, biotin-avidin or biotin-streptavidin, and antibody-antigen. The biotin-avidin combination is preferred.

If a label is used to detect the joined oligonucleotide product, the labels can be attached to either the long or short sequence of one or both probes.

More than two oligonucleotide probes per target nucleic acid molecule can be employed in the process of the present invention to detect different target sequences in the same target nucleic acid molecule. Joined oligonucleotide products from different sequences of the same target nucleic acid molecule can be distinguished from one another, for example, with different labels or by using probes of distinctively different lengths.

In another embodiment of the present invention, the short sequence of the oligonucleotide probe is palindromic. This enables the complementary sequences of the palindrome to hybridize to each other and further protect the chemical functionality group from reacting with other chemical functionality groups when the long and short sequences of the probes are not properly hybridized as described above. Two examples of this embodiment are illustrated below for probe 1. (The double vertical lines in the illustration below merely depicts the demarcation between the long and the short sequence of each probe)

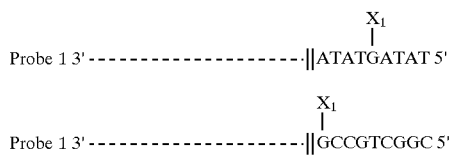

In another embodiment of the present invention, oligonucleotides 1.1, 1.1', 2.1 and 2.1' are provided that are complementary to only the short sequences of probes 1, 1', 2, and 2', respectively. Oligonucleotides 1.1, 1.1', 2.1 and 2.1' do not have chemical functionality groups attached to the sequences. When non-chemically modified oligonucleotides 1.1, 1.1', 2.1 and 2.1' are hybridized to the short sequences of probes 1, 1', 2, and 2', respectively, the non-chemically modified probes further protect the chemical functionality groups on the probes from reacting with each other.

During the denaturation step of the present invention, probes 1, 1', 2, and 2' are denatured from oligonucleotides 1.1, 1.1', 2.1 and 2.1', respectively, and the chemical functionality groups attached to the short sequences of probes 1, 1', 2, and 2' are no longer protected by the oligonucleotides. When probes 1 and 2 hybridize to the target sequence and probes 1' and 2' hybridize to the target complementary sequence, the chemical functionality groups react to form joined oligonucleotide products as described above. An example of this embodiment is illustrated below. (The vertical lines in the illustration below merely depict the demarcation between the long and the short sequence of each probe)

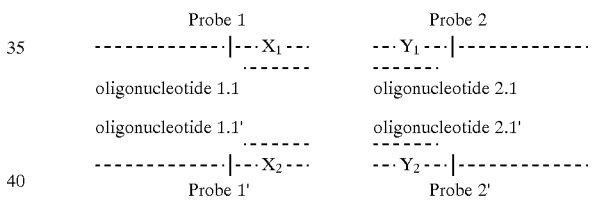

Another generalized illustration of this embodiment depicting a chemical functionality group protected with an unmodified short sequence is shown in FIG. 14.

EXAMPLES

Example 1

This example illustrates the amplification and detection method of the present invention to amplify and detect a 48 base pair DNA sequence contained in the Human Papilloma Virus type 16 (HPV-16) genome. The region to be amplified spans nucleotide base numbers 6634 to 6681 having the sequence:

(See Seedorf, K., et al., *Virology* 145, 181–185 (1985) and SEQ. ID. NOS. 1 (top strand) and 2 (bottom strand).

Four oligonucleotide probes, designated 1, 1', 2 and 2', are used to amplify the above target sequence. The probes have the following sequences. (See SEQ. ID. NOS. 3–6, respectively) The double vertical lines merely depict the demarcation between the long and the short sequences of each probe. The single vertical lines indicate a chemical bond that attaches a chemical functionality group to a substituent group on one of the nucleotides in the short sequence of each probe.

```
Probe 1                                           (SEQ. ID. NO. 3)
3'-AACAACTATGATGTGCGTCATGTT‖ACGATAA-5'
                                 |
                                 X₁
Probe 2                                           (SEQ. ID. NO. 4)
3'-TTATCGT‖TATACAGTAATACACGACGGTATA-5'
         |
         Y₁
Probe 1'                                          (SEQ. ID. NO. 5)
5'-TTGTTGATACTACACGCAGTACAA‖TGCTATT-3'
                                |
                                X₂
Probe 2'                                          (SEQ. ID. NO. 6)
5'-AATAGCA‖ATATGTCATTATGTGCTGCCATAT-3'
         |
         Y₂
```

The oligonucleotide probes of this example are synthesized as follows. First, a guanine residue is modified so that a desired chemical functionality group can later be covalently attached. Conventional methods are then used to synthesize the oligonucleotide probes. During the synthesis of the oligonucleotide, the modified guanine residue is placed in the position of the short sequence where the chemical functionality group is to be located. Once the oligonucleotide probe is synthesized, the appropriate chemical functionality group is attached to the modified guanine residue in the short sequence of the oligonucleotide.

In this example, functionality groups $X_1$ and $X_2$ of probes 1 and 1', respectively, are 2,4,5-trichloro-3-thiophene 1,1-dioxide acetyl. Functionality groups $Y_1$ and $Y_2$ of probes 2 and 2', respectively, are m-maleimidobenzoyl-N-hydroxysulfosuccinimyl ester. Both of these chemical functionality groups are attached to 2'-amino-2'-deoxyguanine in the short sequence of each oligonucleotide probe via their respective N-hydroxysuccinimido derivatives.

The modified guanine residue is obtained by preparing a modified phosphoramidite from 2'-amino-2'-deoxyguanine according to the method described by Benseler, F., et al., in *Nucleosides and Nucleotides* 11, 1333–1351 (1992). The steps in the synthesis of the modified phophoramidite from 2'-amino-2'-deoxyguanine are shown in FIG. 16. Id. at 1348.

All of the oligonucleotides described in Example 1 are synthesized and purified by the following procedure.

I. Automated Synthesis Procedures.

The 2-cyanoethyl phosphoramidites are purchased from Applied Biosystems Inc. The procedure includes condensation of nucleoside phosphoramidites to 30 mg of a nucleoside-derivatized controlled pore glass (CPG) bead support (500 Angstrom pore diameter), using DNA synthesizer from Applied Biosystems Inc., Type 380B-02. The cycles includes detritylation with 2% trichloroacetic acid in dichloromethane; condensation using tetrazol as an activating proton donor; capping with acetic anhydride and dimethylaminopyridine; detritylation using 2% trichloroacetic acid in dichloromethane; and oxidation of the phosphite to the phosphate with 0.1M $I_2/H_2O$/lutidine/tetrahydrofuran. Cycle time is approximately 30 minutes. Yields at each step are essentially quantitative and are determined by collection and spectroscopic examination of the dimethoxytrityl alcohol released during detritylation.

II. Oligodeoxyribonucleotide Deprotection and Purification Procedures

The solid support is removed from the column and exposed to 1 ml concentrated ammonium hydroxide at 60° C. for 16 hours in a closed tube. Ammonia is removed and the residue is applied to a preparative 12% polyacrylamide gel using a Tris-borate buffer (pH 8) containing 7M urea. Electrophoresis is carried out at 20 volts/cm for 5 hours after which the band containing the product is identified by UV shadowing of a fluorescent plate. The band is excised and eluted with 1 ml double distilled water overnight at room temperature. This solution is filtered and the supernatant is extracted (3×300 microliter) with n-butanol. The water phase is placed on a Sephadex G50 column (Pharmacia) (1×10 cm). The elution is monitored by UV absorbance at 260 nm and the appropriate fraction collected, quantitated by UV absorbance in a fixed volume and evaporated to dryness at room temperature in a vacuum centrifuge.

The chemical moiety used to form chemical functionality groups $X_1$ and $X_2$, 2,4,5-trichloro-3-thiophene 1,1-dioxide acetic acid, is prepared according to Brown et al., EP 340,010.

In order to covalently attach 2,4,5-trichloro-3-thiophene 1,1-dioxide acetic acid to the 2'-$NH_2$ substituent group of 2'amino-2'-deoxyguanine, 2,4,5-trichloro-3-thiophene 1,1-dioxide acetic acid must be modified with N-hydroxysuccinimide to yield 2,4,5-trichloro-3-thiophene 1,1-dioxide acetic acid N-hydroxysuccinimide.

2,4,5-trichloro-3-thiophene 1,1-dioxide acetic acid N-hydroxysuccinimide is prepared as follows. 2.45 g (0.01 mole) of 2,4,5-trichloro-3-thiophene 1,1-dioxide acetic acid is dissolved in 100 ml of tetrahydrofuran (THF). To this solution is added 1.3 g (0.015 mole) of N-hydroxysuccinimide (Aldrich) and 2.26 g (0.011 mole) of 1,3-dicyclohexylcarbodiimide (Sigma). The solution is stirred overnight at room temperature. Following filtration of the solution, the solvent is removed under reduced pressure and the white solid product is washed with THF and evaporated to dryness.

The chemical moiety used to form chemical functionality groups $Y_1$ and $Y_2$, m-maleimidobenzoyl-N-hydroxysulfo-succinimide ester, is commercially available. (Pierce)

Chemical modification of the 2'-amino-2'-deoxyguanine residue of each of the oligonucleotide probes to attach functionality groups $X_1$, $X_2$, $Y_1$ and $Y_2$ is performed as follows.

Aliquots of the four oligonucleotide probes containing 2'amino-2'-deoxyguanine having an optical density of 5.0 (5.0 O.D.) are lyophilized to dryness in separate 2ml disposable vials. Each probe preparation is reconstituted in 0.75 ml of 0.2M sodium borate buffer pH 9.3.

To attach chemical functionality groups $X_1$ and $X_2$, 0.25 ml of 2,4,5-trichloro-3-thiophene 1,1-dioxide acetic acid N-hydroxysuccinimide (see above synthesis) dissolved in N,N-dimethylformamide (DMF) at 20 mg/ml is added to each of the vials containing modified probes 1 and 1'.

To attach chemical functionality groups $Y_1$ and $Y_2$, 0.25 ml of m-maleimidobenzoyl-N-hydroxysulfo-succinimide ester at 20 mg/ml is added to each of the vials containing modified probes 2 and 2'.

The reaction mixture in each of the vials is agitated vigorously at room temperature (RT) for approximately 12 hours. The mixtures are then centrifuged and each passed through a separate Pharmacia Sephadex NAP-10 column to desalt the solutions and remove excess chemical functionality group reagent. Each of the resulting solutions are purified with an FPLC column (Pharmacia). The FPLC system is equipped with a Pro RPC HR 10/10 column (100 mm×10 mm diameter, packed with a silica-based 13 μm C2/C8 matrix of 300 Å pore size) The solutions are purified by using a linear gradient of acetonitrile/10 mM triethylammonium acetate 1:1 (v/v) against 10 mM triethylammonium acetate ranging from 0 to 35% over 45 minutes at a rate of 2 ml/min.

Fractions are collected and pooled for each purified oligonucleotide probe. Each of the probes, 1, 1', 2 and 2', are lyophilized to dryness and stored at 4° C. until use.

Figure 7:
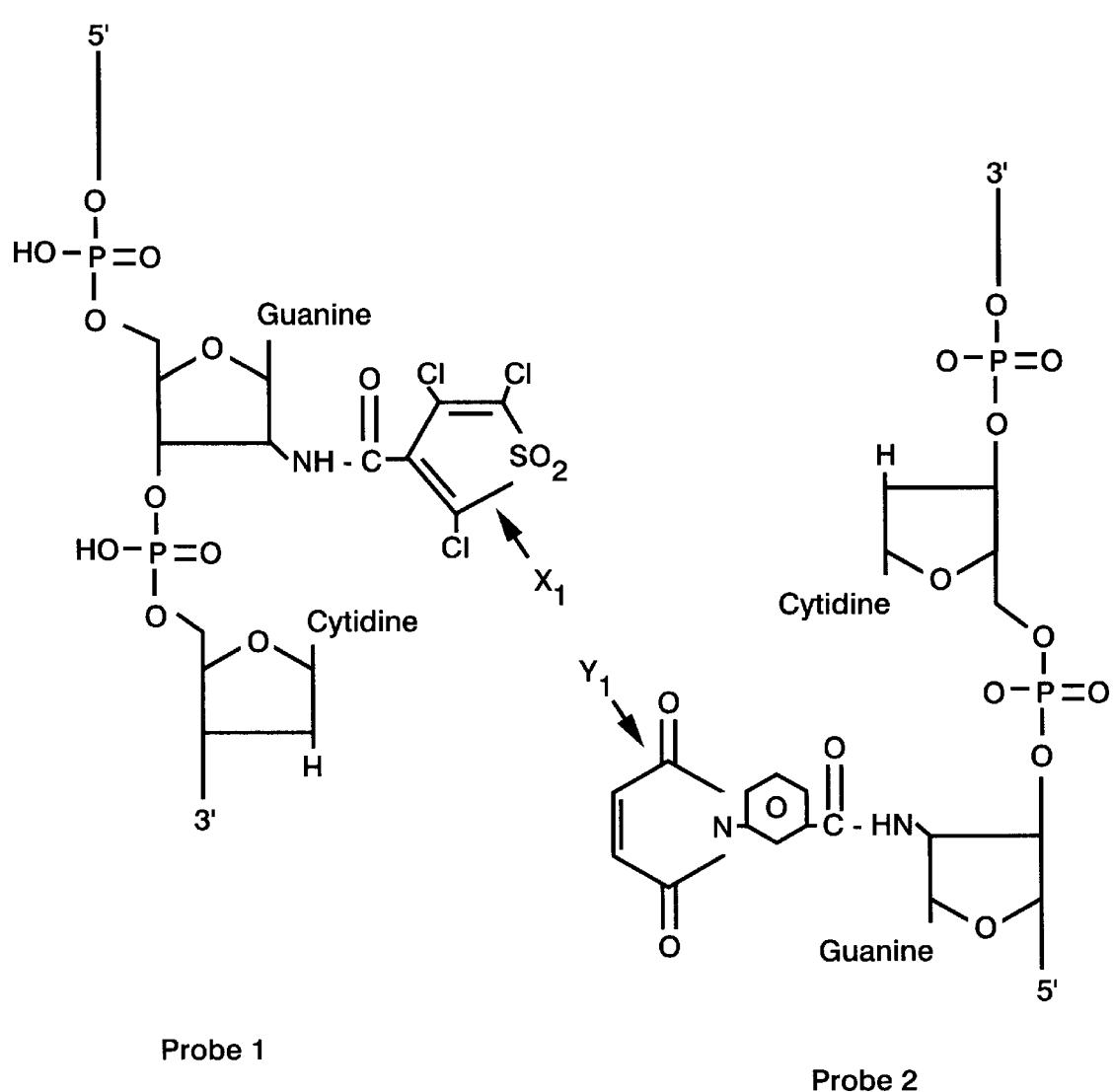
FIG. 7 shows a segment of two nucleotides from short sequences I and K of probes 1 and 2, respectively, with chemical functionality groups $X_1$ and $Y_1$ attached to guanine residues.
Figure 8:
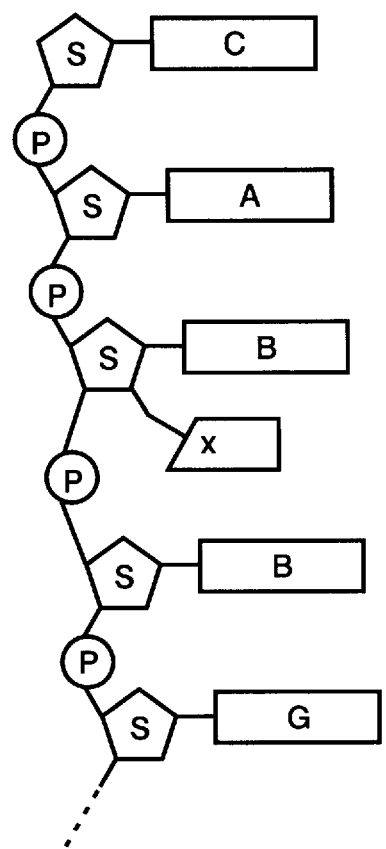
FIG. 8 shows a generalized illustration of a protected chemical functionality group X attached to the sugar moiety of nucleotide base B in the short sequence of a probe. In the Figure, X represents a chemical functionality group, A represents adenine, G represents guanine, C represents cytidine, B represents any nucleotide base and the string of symbols with S or P inside represents the sugar-phosphate backbone of the nucleic acid sequence.

An illustration of the modified guanine residues and an adjacent cytosine residue of the short sequences of probes 1, 1', 2, and 2' is shown in FIG. 7.

Amplification of the HPV-16 sequence shown above (SEQ. ID. NOS. 1–2) is performed as follows.

The HPV-16 sequence is contained in a plasmid. The plasmid is prepared by cloning the HPV-16 sequence published by Seedorf et al., in *Virology* 145, 181–185 (1985) in a blue script vector (Stratagene). Once the HPV-16 sequence is cloned into the plasmid, the plasmid is dissolved in double distilled water at a concentration of 20 ng/ml.

$10^{11}$ molecules of each of the oligonucleotide probes are reconstituted in hybridization buffer at a final volume of 200 μl. The hybridization buffer contains 30% deionized formamide in water (vol/vol), 0.54M NaCl, 0.03M sodium phosphate (pH 7.4), 0.003M EDTA, 5% dextran sulfate 500K m.w. (Sigma)(w/vol) and 0.1% Triton X-100.

Deionized formamide is prepared by adding 1 gm of Bio-Rad AG 501-X8(D) 20–50 mesh mixed bed resin to 50 ml of formamide (Sigma Chemical Co.) and mixing for 30 minutes at room temperature. The formamide is filtered twice through Whatman No. 1 filter paper.

Two reaction tubes (Perkin Elmer), 1 and 2, are used for the amplification reaction. Tube 1 is used for the control and tube 2 is used for the test reaction. Tube 1 contains no target sequence. Tube 2 contains a sample of HPV-16 target sequence.

100 μl of the hybridization buffer containing the four oligonucleotide probes, 1, 1', 2, and 2', is added to each tube. 1 μl of the solution containing the plasmid with the HPV-16 sequence, described above, is added to tube 2. 1 μl of triple distilled water is added to tube 1 as a control. The solutions in each tube are briefly mixed by gently vortexing the tubes. 100 μl of mineral oil is slowly added to each tube to form a layer on top of the reaction mixture to prevent evaporation of the solutions during the repeated heating cycles of the amplification reaction.

Both tubes are placed in a DNA thermal cycler (Perkin Elmer, Cetus) and subjected to 40 heating and cooling cycles. Each cycle consists of a 65 second incubation at 90° C and a 240 second incubation at 40° C.

After cycling, 20 μl of each solution is added to a mixture of 2 μl bromphenol blue and 40% glycerol in 1M TBE (Tris borate EDTA). Each tube is gently mixed by vortex mixing.

The amplified HPV-16 target sequence is detected by ethidium bromide staining of the joined oligonucleotide product on a gel. 20 μl of each solution is loaded onto a 12% polyacrylamide gel using tris-borate buffer (pH 8.0).

Electrophoresis is carried out at 20 volts/cm for three hours, after which the gel is immersed in a 100 ml solution of ethidium bromide, 0.5 μg/ml $H_2O$, for 45 minutes at room temperature.

The gel is exposed to Polaroid photographic film, type 57 or 667 (ASA 3000) with an efficient ultra-violet (UV) light source (72,500 μW/cm$^2$). The photographic film is exposed for 0.5 second at f8 to detect bands of joined oligonucleotide product in amounts as small as 10 ng.

GLOSSARY $A_1$ represents adenine with a chemical functionality group Z replacing a hydrogen from the amino group located at the C-6 position $A_2$ represents adenine with a chemical functionality group Z attached to the hydroxyl group located at the C-2' position of the ribose ring $A_3$ represents adenine with chemical functionality group Z replacing the hydrogen located at the C-8 position $A_4$ represents adenine with chemical functionality group Z replacing the hydroxyl group located at the C-2' position of the ribose ring B represents any nucleotide base $C_1$ represents cytidine with a chemical functionality group Z replacing a hydrogen from the amino group located at the C-6 position $C_2$ represents cytidine with a chemical functionality group Z attached to the hydroxyl group located at the C-2' position of the ribose ring $C_3$ represents cytidine with a chemical functionality group Z replacing the hydroxyl group located at the C-2' position of the ribose ring D represents modified nucleotides $A_4$, $C_3$, $G_3$, $T_3$ or $U_1$ E represents modified nucleotides $A_1$ or $C_1$ F represents modified nucleotides $A_3$ or $G_1$ $G_1$ represents guanine with chemical functionality group Z replacing the hydrogen located at the C-8 position $G_2$ represents guanine with a chemical functionality group Z attached to the hydroxyl group located at the C-2' position of the ribose ring $G_3$ represents guanine with chemical functionality group Z replacing the hydroxyl group located at the C-2' position of the ribose ring H and H' represent the long sequence of probes 1 and 1', respectively I and I' represent the short sequence of probes 1 and 1', respectively J and J' represent the long sequence of probes 2 and 2', respectively K and K' represent the short sequence of probes 2 and 2', respectively L represents modified nucleotides $A_2$, $C_2$, $G_2$, $T_2$ and $U_2$ R and R' represent any of the modified nucleotides shown in FIGS. 2–6

$T_1$ represents thymidine with chemical functionality group Z replacing a hydrogen from the methyl group located at the C-5 position $T_2$ represents thymidine with a chemical functionality group Z attached to the hydroxyl group located at the C-2' position of the ribose ring $T_3$ represents thymidine with chemical functionality group Z replacing the hydroxyl group located at the C-2' position of the ribose ring $U_1$ represents uridine with chemical functionality group Z replacing the hydroxyl group located at the C-2' position of the ribose ring $U_2$ represents uridine with a chemical functionality group Z attached to the hydroxyl group located at the C-2' position of the ribose ring X represents chemical functionality groups $X_1$ or $X_2$ $X_1$ represents a chemical functionality group attached to the short sequence of probe 1

$X_2$ represents a chemical functionality group attached to the short sequence of probe 1'

Y represents chemical functionality groups $Y_1$ or $Y_2$ $Y_1$ represents a chemical functionality group attached to the short sequence of probe 2

$Y_2$ represents a chemical functionality group attached to the short sequence of probe 2'

Z represents chemical functionality groups $X_1$, $X_2$, $Y_1$ or $Y_2$

What is claimed is:

1. A process for amplifying and detecting, in a sample, a single stranded target nucleic acid molecule comprising a target sequence or a double stranded nucleic acid target molecule comprising a target sequence and target complementary sequence, the process comprising the steps of:
  (a) providing a first oligonucleotide complement pair and a second oligonucleotide complement pair, wherein:
    (i) the first oligonucleotide complement pair consists of a probe 1 and a probe 1' and the second oligonucleotide complement pair consists of a probe 2 and a probe 2';
    (ii) probe 1 comprises a long sequence H and a short sequence I; probe 1' comprises a long sequence H' and a short sequence I';
    (iii) probe 2 comprises a long sequence J and a short sequence K; probe 2' comprises a long sequence J' and a short sequence K';
    (iv) long sequence H of probe 1 and long sequence H' of probe 1' are complementary to each other;
    (v) long sequence J of probe 2 and long sequence J' of probe 2' are complementary to each other;
    (vi) long sequence H of probe 1 and long sequence J of probe 2 are complementary to adjacent portions of the target sequence;
    (vii) long sequence H' of probe 1' and long sequence J' of probe 2' are complementary to adjacent portions of the target complementary sequence;
    (viii) short sequence I and short sequence K do not hybridize to the target sequence when long sequence H and long sequence J hybridize to the target sequence;
    (ix) short sequence I' and short sequence K' do not hybridize to the target complementary sequence when long sequence H' and long sequence J' hybridize to the target complementary sequence;
    (x) short sequence I of probe 1 is complementary to short sequence K of probe 2 and short sequence I' of probe 1' is complementary to short sequence K' of probe 2';
    (xi) the sugar or base moiety of one or more nucleotides of sequence I of probe 1 is modified with chemical functionality group $X_1$; the sugar or base moiety of one or more nucleotides of sequence K of probe 2 is modified with chemical functionality group $Y_1$; chemical functionality group $X_1$ is reactive with chemical functionality group $Y_1$;
    (xii) the sugar or base moiety of one or more nucleotides of sequence I' of probe 1' is modified with chemical functionality group $X_2$; the sugar or base moiety of one or more nucleotides of sequence K' of probe 2' is modified with chemical functionality group $Y_2$; chemical functionality group $X_2$ is reactive with chemical functionality group $Y_2$;

(xiii) short sequence I hybridizes to short sequence K when long sequence H of probe 1 and long sequence J of probe 2 hybridize to adjacent portions of the target sequence;

(xiv) when short sequence I hybridizes to short sequence K, chemical functionality group $X_1$ reacts with chemical functionality group $Y_1$ to form a chemical bond;

(xv) short sequence I' hybridizes to short sequence K' when long sequence H' of probe 1' and long sequence J' of probe 2' hybridize to adjacent portions of a target complementary sequence;

(xvi) when short sequence I' hybridizes to short sequence K', chemical functionality group $X_2$ reacts with chemical functionality group $Y_2$ to form a chemical bond;

(b) hybridizing long sequence H of probe 1 and long sequence J of probe 2 to adjacent portions of the target sequence and hybridizing long sequence H' of probe 1' and long sequence J' of probe 2' to adjacent portions of the target complementary sequence;

(c) joining probe 1 and probe 2, hybridized after step (b) to adjacent portions of the target sequence, to each other by forming a chemical bond between chemical functionality groups $X_1$ and $Y_1$, thereby forming a first joined oligonucleotide product having the target complementary sequence;

(d) joining probe 1' and probe 2', hybridized after step (b) to adjacent portions of the target complementary sequence, to each other by forming a chemical bond between chemical functionality groups $X_2$ and $Y_2$, thereby forming a second joined oligonucleotide product having the target sequence;

(e) treating the sample under denaturing conditions;

(f) repeating steps (b) through (e) a desired number of times; and (g) detecting the joined oligonucleotide products.

2. A process for linear amplification and detection, in a sample, of a single stranded target nucleic acid molecule comprising a target sequence or a double stranded nucleic acid target molecule comprising a target sequence and target complementary sequence, the process comprising the steps of:

(a) providing an oligonucleotide pair, wherein:

(i) the oligonucleotide pair consists of a probe 1 and a probe 2 or a probe 1' and a probe 2';

(ii) probe 1 comprises a long sequence H and a short sequence I; probe 2 comprises a long sequence J and a short sequence K;

(iii) probe 1' comprises a long sequence H' and a short sequence I'; probe 2' comprises a long sequence J' and a short sequence K';

(iv) long sequence H of probe 1 and long sequence J of probe 2 are complementary to adjacent portions of the target sequence;

(v) long sequence H' of probe 1' and long sequence J' of probe 2' are complementary to adjacent portions of the target complementary sequence;

(vi) short sequence I and short sequence K do not hybridize to the target sequence when long sequence H and long sequence J hybridize to the target sequence;

(vii) short sequence I' and short sequence K' do not hybridize to the target complementary sequence when long sequence H' and long sequence J' hybridize to the target complementary sequence;

(viii) short sequence I of probe 1 is complementary to short sequence K of probe 2 and short sequence I' of probe 1' is complementary to short sequence K' of probe 2';

(ix) the sugar or base moiety of one or more nucleotides of sequence I of probe 1 is modified with chemical functionality group $X_1$; the sugar or base moiety of one or more nucleotides of sequence K of probe 2 is modified with chemical functionality group $Y_1$; chemical functionality group $X_1$ is reactive with chemical functionality group $Y_1$;

(x) the sugar or base moiety of one or more nucleotides of sequence I' of probe 1' is modified with chemical functionality group $X_2$; the sugar or base moiety of one or more nucleotides of sequence K' of probe 2' is modified with chemical functionality group $Y_2$; chemical functionality group $X_2$ is reactive with chemical functionality group $Y_2$;

(xi) short sequence I hybridizes to short sequence K when long sequence H of probe 1 and long sequence J of probe 2 hybridize to adjacent portions of the target sequence;

(xii) when short sequence I hybridizes to short sequence K, chemical functionality group $X_1$ reacts with chemical functionality group $Y_1$ to form a chemical bond;

(xiii) short sequence I' hybridizes to short sequence K' when long sequence H' of probe 1' and long sequence J' of probe 2' hybridize to adjacent portions of a target complementary sequence;

(xiv) when short sequence I' hybridizes to short sequence K', chemical functionality group $X_2$ reacts with chemical functionality group $Y_2$ to form a chemical bond;

(b) hybridizing long sequence H of probe 1 and long sequence J of probe 2 to adjacent portions of the target sequence or hybridizing long sequence H' of probe 1' and long sequence J' of probe 2' to adjacent portions of the target complementary sequence;

(c) joining probe 1 and probe 2, hybridized after step (b) to adjacent portions of the target sequence, to each other by forming a chemical bond between chemical functionality groups $X_1$ and $Y_1$, thereby forming a joined oligonucleotide product having the target complementary sequence; or (d) joining probe 1' and probe 2', hybridized after step (b) to adjacent portions of the target complementary sequence, to each other by forming a chemical bond between chemical functionality groups $X_2$ and $Y_2$, thereby forming a joined oligonucleotide product having the target sequence;

(e) treating the sample under denaturing conditions;

(f) repeating steps (b) through (e) a desired number of times; and (g) detecting the joined oligonucleotide products.

3. The process of claim 1 or 2 wherein chemical functionality group $X_1$ is an electrophile and chemical functionality group $Y_1$ is a nucleophile.

4. The process of claim 1 or 2 wherein chemical functionality group $X_1$ is a nucleophile and chemical functionality group $Y_1$ is an electrophile.

5. The process of claim 1 or 2 wherein chemical functionality group $X_2$ is an electrophile and chemical functionality group $Y_2$ is a nucleophile.

6. The process of claim 1 or 2 wherein chemical functionality group $X_2$ is a nucleophile and chemical functionality group $Y_2$ is an electrophile.

7. The process of claim 1 or 2 wherein chemical functionality group $X_1$, $X_2$, $Y_1$ or $Y_2$ replaces the hydroxyl group located at the C-2' position of the ribose ring of a nucleotide in short sequence I, I', K or K', respectively.

8. The process of claim 1 or 2 wherein chemical functionality group $X_1$, $X_2$, $Y_1$ or $Y_2$ replaces the hydrogen in the hydroxyl group located at the C-2' position of the ribose ring of a nucleotide in short sequence I, I', K or K', respectively.

9. The process of claim 1 or 2 wherein chemical functionality group $X_1$, $X_2$, $Y_1$ or $Y_2$ replaces a hydrogen in the amino group located at the C-6 position of an adenine or cytidine residue in short sequence I, I', K or K', respectively.

10. The process of claim 1 or 2 wherein chemical functionality group $X_1$, $X_2$, $Y_1$ or $Y_2$ replaces the hydrogen located at the C-8 position of an adenine or guanine residue in short sequence I, I', K or K', respectively.

11. The process of claim 1 or 2 wherein chemical functionality group $X_1$, $X_2$, $Y_1$ or $Y_2$ replaces a hydrogen from the methyl group located at the C-5 position of a thymidine residue in short sequence I, I', K or K', respectively.

12. The process of claim 1 or 2 wherein the nucleic acid sequence of short sequence I, I', K or K' is palindromic.

13. The process of claim 1 or 2 wherein chemical functionality group $X_1$, $X_2$, $Y_1$ or $Y_2$ in short sequence I, I', K or K', respectively, of probes 1, 2, 1' or 2', respectively, is protected by oligonucleotide 1.1, 2.1, 1.1' or 2.1', respectively.

14. The process of claim 1 or 2 wherein the ratio of the length of the long sequence to the length of the short sequence of probes 1, 2, 1', or 2' is from 2:1 to 50:1.

15. The process of claim 1 or 2 wherein the ratio of the length of the long sequence to the length of the short sequence is 2:1.

16. The process of claim 1 or 2 wherein the ratio of the length of the long sequence to the length of the short sequence is 3:1.

17. The process of claim 1 or 2 wherein the ratio of the length of the long sequence to the length of the short sequence is 5:1.

18. The process of claim 1 or 2 wherein the ratio of the length of the long sequence to the length of the short sequence is 10:1.

19. The process of claim 1 or 2 wherein the ratio of the length of the long sequence to the length of the short sequence is 20:1.

20. The process of claim 1 or 2 wherein the reaction between chemical functionality groups $X_1$ and $Y_1$ or $X_2$ and $Y_2$ is the substitution of a nucleophile for an electrophilic leaving group.

21. The process of claim 1 or 2 wherein the reaction between chemical functionality groups $X_1$ and $Y_1$ or $X_2$ and $Y_2$ is a Michael addition reaction.

22. The process of claim 1 or 2 wherein the reaction between chemical functionality groups $X_1$ and $Y_1$ or $X_2$ and $Y_2$ is a Diels-Alder reaction.

23. The process of claim 1 or 2 wherein the reaction between chemical functionality groups $X_1$ and $Y_1$ or $X_2$ and $Y_2$ is the addition of a thiol group to the double bond of a maleimido moiety.

24. The process of claim 1 or 2 wherein the reaction between chemical functionality groups $X_1$ and $Y_1$ or $X_2$ and $Y_2$ is a photochemical reaction.

25. The process of claim 1 or 2 wherein the reaction between chemical functionality groups $X_1$ and $Y_1$ or $X_2$ and $Y_2$ is a [2+2] photocyclodimerization reaction.

26. The process of claim 1 or 2, wherein the oligonucleotide pairs are present as a molar excess in the range of $10^5$ to $10^{15}$ pairs per nucleic acid target sequence or target complementary sequence.

* * * * *